United States Patent
Nguyen et al.

(10) Patent No.: US 11,406,502 B2
(45) Date of Patent: Aug. 9, 2022

(54) ORTHOPEDIC IMPLANTS AND METHODS

(71) Applicant: Optimotion Implants LLC, Orlando, FL (US)

(72) Inventors: Vuong Binh Nguyen, Windermere, FL (US); Daniel F. Justin, Orlando, FL (US)

(73) Assignee: OPTIMOTION IMPLANTS LLC, Orlando, FL (US)

( * ) Notice: Subject to any disclaimer, the term of this patent is extended or adjusted under 35 U.S.C. 154(b) by 340 days.

(21) Appl. No.: 16/505,595

(22) Filed: Jul. 8, 2019

(65) Prior Publication Data

US 2019/0343639 A1   Nov. 14, 2019

Related U.S. Application Data

(63) Continuation-in-part of application No. 15/622,688, filed on Jun. 14, 2017, now Pat. No. 10,905,436.
(Continued)

(51) Int. Cl.
| A61F 2/30 | (2006.01) |
| A61F 2/38 | (2006.01) |
| A61F 2/46 | (2006.01) |

(52) U.S. Cl.
CPC ........ *A61F 2/30767* (2013.01); *A61F 2/3094* (2013.01); *A61F 2/3872* (2013.01);
(Continued)

(58) Field of Classification Search
CPC ........ A61F 2/389; A61F 2/38; A61F 2/30734; A61F 2/30767; A61F 2002/30604; A61F 2002/3092; A61F 2002/30968
(Continued)

(56) References Cited

U.S. PATENT DOCUMENTS

| 4,257,129 A | 3/1981 | Volz |
| 4,293,963 A | 10/1981 | Gold et al. |

(Continued)

FOREIGN PATENT DOCUMENTS

| CN | 101732761 | 6/2010 |
| GB | 2388034 | 11/2003 |
| WO | WO2012021764 | 2/2012 |

OTHER PUBLICATIONS

Blair et al., "Rapid Solid-State Synthesis of Titanium Aluminides", *American Chemical Society*, Chem Mater., Jan. 9, 2003 (8 pages).
(Continued)

*Primary Examiner* — Marcela I. Shirsat
(74) *Attorney, Agent, or Firm* — David Meibos; Maywood IP Law

(57) ABSTRACT

A prosthesis for replacing a natural articular surface on a bone may have a joint facing side with an articular surface, a bone anchoring side with a bone engagement surface, and a bone engagement pad secured to at least part of the bone engagement surface. The bone engagement pad may have a transverse portion extending transverse to a length of the bone, and one or more protruding portions extending generally perpendicular to the transverse portion. The transverse portion may have a pad bone-facing surface with a first porosity level, and a pad joint-facing surface on an opposite side of the transverse portion from the pad bone-facing surface, with a second, lower porosity level. The bone engagement surface may be formed via a first manufacturing process selected from the group consisting of forging, milling, and casting. The bone engagement pad may be formed via an additive manufacturing process.

25 Claims, 10 Drawing Sheets

Related U.S. Application Data

(60) Provisional application No. 62/694,834, filed on Jul. 6, 2018, provisional application No. 62/466,249, filed on Mar. 2, 2017.

(52) U.S. Cl.
CPC .......... *A61F 2/30734* (2013.01); *A61F 2/389* (2013.01); *A61F 2/3859* (2013.01); *A61F 2/4644* (2013.01); *A61F 2002/3092* (2013.01); *A61F 2002/30604* (2013.01); *A61F 2002/30968* (2013.01); *A61F 2310/00023* (2013.01)

(58) Field of Classification Search
USPC .......... 623/20.35, 20.36, 22.4, 22.41, 23.11, 623/23.12, 20.29; 606/89
See application file for complete search history.

(56) References Cited

U.S. PATENT DOCUMENTS

| | | |
|---|---|---|
| 4,323,756 A | 4/1982 | Brown et al. |
| 4,524,766 A | 6/1985 | Petersen |
| 4,714,474 A | 12/1987 | Brooks, Jr. et al. |
| 4,822,366 A | 4/1989 | Bolesky |
| 4,936,847 A | 6/1990 | Manginelli |
| 4,938,762 A | 7/1990 | Wehrli |
| 4,944,757 A | 7/1990 | Martinez et al. |
| 4,946,379 A | 8/1990 | Berchem |
| 4,960,643 A | 10/1990 | Lemelson |
| 4,963,152 A | 10/1990 | Hofmann et al. |
| 5,007,933 A | 4/1991 | Sidebotham et al. |
| 5,047,058 A | 9/1991 | Roberts et al. |
| 5,059,216 A | 10/1991 | Winters |
| 5,100,409 A | 3/1992 | Coates et al. |
| 5,147,405 A | 9/1992 | Van Zile et al. |
| 5,176,684 A | 1/1993 | Ferrante et al. |
| 5,192,328 A | 3/1993 | Winters |
| 5,201,881 A | 4/1993 | Evans |
| 5,226,915 A | 7/1993 | Bertin |
| 5,330,534 A | 7/1994 | Herrington et al. |
| 5,354,414 A | 10/1994 | Feygin |
| 5,415,662 A | 5/1995 | Ferrante et al. |
| 5,531,793 A | 7/1996 | Kelman et al. |
| 5,549,685 A | 8/1996 | Hayes |
| 5,569,259 A | 10/1996 | Ferrante et al. |
| 5,609,645 A | 3/1997 | Vinciguerra |
| 5,653,714 A | 8/1997 | Dietz et al. |
| 5,658,334 A | 8/1997 | Caldarise et al. |
| 5,658,341 A | 8/1997 | Delfosse |
| 5,658,344 A | 8/1997 | Hurlburt |
| 5,672,284 A | 9/1997 | Devanathan et al. |
| 5,681,316 A | 10/1997 | DeOrio et al. |
| 5,683,397 A | 11/1997 | Vendrely et al. |
| 5,687,788 A | 11/1997 | Caldarise et al. |
| 5,702,460 A | 12/1997 | Carls et al. |
| 5,702,463 A | 12/1997 | Pothier et al. |
| 5,716,412 A | 2/1998 | DeCarlo, Jr. et al. |
| 5,755,808 A | 5/1998 | DeCarlo et al. |
| 5,762,125 A | 6/1998 | Mastrorio |
| 5,824,100 A | 10/1998 | Kester et al. |
| 5,824,103 A | 10/1998 | Williams |
| 5,879,393 A | 3/1999 | Whiteside et al. |
| 5,879,394 A | 3/1999 | Ashby et al. |
| 5,897,592 A | 4/1999 | Caldarise et al. |
| 5,910,173 A | 6/1999 | DeCarlo, Jr. et al. |
| 5,964,808 A | 10/1999 | Blaha et al. |
| 5,980,974 A | 11/1999 | Armini et al. |
| 6,004,352 A | 12/1999 | Buni |
| 6,074,424 A | 6/2000 | Perrone, Jr. et al. |
| 6,087,553 A | 7/2000 | Cohen et al. |
| 6,105,235 A | 8/2000 | Caldarise |
| 6,132,674 A | 10/2000 | Compton et al. |
| 6,165,221 A | 12/2000 | Schmotzer |
| 6,165,223 A | 12/2000 | Metzger et al. |
| RE37,277 E | 7/2001 | Baldwin et al. |
| 6,258,127 B1 | 7/2001 | Schmotzer |
| 6,506,216 B1 | 1/2003 | McCue et al. |
| 6,652,588 B2 | 11/2003 | Hayes, Jr. et al. |
| 6,827,739 B2 | 12/2004 | Griner et al. |
| 6,858,032 B2 | 2/2005 | Chow et al. |
| 6,869,448 B2 | 3/2005 | Tuke et al. |
| 6,896,702 B2 | 5/2005 | Collazo |
| 6,923,832 B1 | 8/2005 | Sharkey et al. |
| 6,945,448 B2 | 9/2005 | Medlin et al. |
| 6,974,625 B2 | 12/2005 | Hunter et al. |
| 7,001,672 B2 | 2/2006 | Justin et al. |
| 7,081,137 B1 | 7/2006 | Servidio |
| 7,087,200 B2 | 8/2006 | Taboas et al. |
| 7,105,030 B2 | 9/2006 | Despres, III et al. |
| 7,160,330 B2 | 1/2007 | Axelson, Jr. et al. |
| 7,175,665 B2 | 2/2007 | German et al. |
| 7,182,786 B2 | 2/2007 | Justin et al. |
| 7,189,262 B2 | 3/2007 | Hayes, Jr. et al. |
| 7,258,810 B2 | 8/2007 | Hunter et al. |
| 7,294,149 B2 | 11/2007 | Hozack et al. |
| 7,309,339 B2 | 12/2007 | Cusick et al. |
| 7,357,817 B2 | 4/2008 | D'Alessio, II |
| 7,413,577 B1 | 8/2008 | Servidio |
| 7,445,640 B2 | 11/2008 | Despres, III et al. |
| 7,497,874 B1 | 3/2009 | Metzger et al. |
| 7,513,912 B2 | 4/2009 | Hayes, Jr. et al. |
| 7,524,334 B2 | 4/2009 | Haidukewych |
| 7,537,664 B2 | 5/2009 | O'Neill et al. |
| 7,578,851 B2 | 8/2009 | Dong et al. |
| 7,625,407 B2 | 12/2009 | Akizuki et al. |
| 7,628,817 B1 | 12/2009 | Axelson, Jr. et al. |
| 7,632,575 B2 | 12/2009 | Justin et al. |
| 7,648,735 B2 | 1/2010 | Hunter et al. |
| 7,666,522 B2 | 2/2010 | Justin et al. |
| 7,771,484 B2 | 8/2010 | Campbell |
| 7,837,690 B2 | 11/2010 | Metzger |
| 7,842,092 B2 | 11/2010 | Otto et al. |
| 7,850,862 B2 | 12/2010 | Amrich et al. |
| 7,857,858 B2 | 12/2010 | Justin et al. |
| 7,883,510 B2 | 2/2011 | Kim et al. |
| 7,887,542 B2 | 2/2011 | Metzger et al. |
| 7,918,382 B2 | 4/2011 | Charlebois et al. |
| 7,938,833 B2 | 5/2011 | Bastian |
| 7,963,968 B2 | 6/2011 | Dees, Jr. |
| 8,038,681 B2 | 10/2011 | Koenemann |
| 8,070,821 B2 | 12/2011 | Roger |
| 8,075,628 B2 | 12/2011 | Justin et al. |
| 8,142,886 B2 | 3/2012 | Noble et al. |
| 8,147,861 B2 | 4/2012 | Jones et al. |
| 8,162,949 B2 | 4/2012 | Duggineni et al. |
| 8,167,954 B2 | 5/2012 | Despres, III et al. |
| 8,187,335 B2 | 5/2012 | Wyss et al. |
| 8,191,760 B2 | 6/2012 | Charlebois et al. |
| 8,192,498 B2 | 6/2012 | Wagner et al. |
| 8,236,061 B2 | 8/2012 | Heldreth et al. |
| 8,241,367 B2 | 8/2012 | Justin et al. |
| 8,268,006 B2 | 9/2012 | Meyers et al. |
| 8,268,099 B2 | 9/2012 | O'Neill et al. |
| 8,268,100 B2 | 9/2012 | O'Neill et al. |
| 8,350,186 B2 | 1/2013 | Jones et al. |
| 8,357,201 B2 | 1/2013 | Mayer et al. |
| 8,388,887 B2 | 3/2013 | Gupta et al. |
| 8,403,992 B2 | 3/2013 | Otto et al. |
| 8,403,994 B2 | 3/2013 | Maloney et al. |
| 8,414,908 B2 | 4/2013 | Jin et al. |
| 8,449,618 B2 | 5/2013 | Otto et al. |
| 8,518,047 B2 | 8/2013 | Metzger et al. |
| 8,551,100 B2 | 10/2013 | Metzger |
| 8,556,981 B2 | 10/2013 | Jones et al. |
| 8,562,688 B2 | 10/2013 | Belcher |
| 8,603,178 B2 | 12/2013 | Otto et al. |
| 8,632,600 B2 | 1/2014 | Zannis et al. |
| 8,663,337 B2 | 3/2014 | Anderson et al. |
| 8,668,743 B2 | 3/2014 | Perler |
| 8,690,954 B2 | 4/2014 | Parisi et al. |
| 8,702,803 B2 | 4/2014 | Otto et al. |
| 8,715,359 B2 * | 5/2014 | Deffenbaugh .......... A61F 2/389 623/20.29 |

(56) References Cited

U.S. PATENT DOCUMENTS

| | | |
|---|---|---|
| 8,728,387 B2 | 5/2014 | Jones et al. |
| 8,735,773 B2 | 5/2014 | Lang |
| 8,758,444 B2 | 6/2014 | Wentorf et al. |
| 8,764,759 B2 | 7/2014 | Dees, Jr. |
| 8,771,280 B2 | 7/2014 | Bailey et al. |
| 8,784,496 B2 | 7/2014 | Wagner et al. |
| 8,790,345 B2 | 7/2014 | Anderson |
| 8,795,380 B2 | 8/2014 | Heldreth et al. |
| 8,828,086 B2 | 9/2014 | Williams et al. |
| 8,834,575 B2 | 9/2014 | Wyss et al. |
| 8,843,229 B2 | 9/2014 | Vanasse et al. |
| 8,870,883 B2 | 10/2014 | Metzger et al. |
| 8,900,316 B2 | 12/2014 | Lenz et al. |
| 8,900,317 B2 | 12/2014 | Zubok et al. |
| 8,951,465 B2 | 2/2015 | Gupta |
| 8,968,413 B2 | 3/2015 | Cook et al. |
| 8,985,430 B2 | 3/2015 | Charlebois et al. |
| 8,986,310 B2 | 3/2015 | Bailey et al. |
| 8,992,703 B2 | 3/2015 | O'Neill et al. |
| 9,023,053 B2 | 5/2015 | Metzger |
| 9,044,249 B2 | 6/2015 | Dees, Jr. |
| 9,072,605 B2 | 7/2015 | Coon et al. |
| 9,119,734 B2 | 9/2015 | Dees |
| 9,149,287 B2 | 10/2015 | Bailey et al. |
| 9,161,761 B2 | 10/2015 | Metzger et al. |
| 9,186,255 B2 | 11/2015 | Parisi et al. |
| 9,192,459 B2 | 11/2015 | Bonutti |
| 9,220,601 B2 | 12/2015 | Williams et al. |
| 9,226,827 B2 | 1/2016 | Luscher |
| 9,237,950 B2 | 1/2016 | Hensley et al. |
| 9,265,613 B2 | 2/2016 | Nevins et al. |
| 9,278,003 B2 | 3/2016 | Deffenbaugh et al. |
| 9,287,301 B2 | 3/2016 | Tohyama |
| 9,301,846 B2 | 4/2016 | Landon |
| 9,320,605 B2 | 4/2016 | Otto et al. |
| 9,326,864 B2 | 5/2016 | Wyss et al. |
| 9,370,605 B2 | 6/2016 | Zhang et al. |
| 9,381,085 B2 | 7/2016 | Axelson, Jr. et al. |
| 9,387,084 B2 | 7/2016 | Masini et al. |
| 9,402,729 B2 | 8/2016 | Otto et al. |
| 9,408,699 B2 | 8/2016 | Stalcup et al. |
| 9,427,334 B2 | 8/2016 | Axelson, Jr. et al. |
| 9,445,823 B2 | 9/2016 | Harris et al. |
| 9,445,902 B2 | 9/2016 | Klein et al. |
| 9,445,909 B2 | 9/2016 | Cohen et al. |
| 9,452,051 B2 | 9/2016 | Collazo et al. |
| 9,452,053 B2 | 9/2016 | Wagner et al. |
| 9,456,901 B2 | 10/2016 | Jones et al. |
| 9,480,511 B2 | 11/2016 | Butters et al. |
| 9,517,134 B2 | 12/2016 | Lang |
| 9,517,138 B2 | 12/2016 | Zubok et al. |
| 9,539,099 B2 | 1/2017 | Heldreth et al. |
| 9,554,862 B2 | 1/2017 | Davignon et al. |
| 9,566,161 B2 | 2/2017 | Hartdegen et al. |
| 9,579,210 B2 | 2/2017 | Wong |
| 9,636,229 B2 | 5/2017 | Lang et al. |
| 9,642,711 B2 | 5/2017 | Carson |
| 9,649,195 B2 | 5/2017 | Bechtold et al. |
| 9,649,205 B2 | 5/2017 | Dees, Jr. |
| 9,655,632 B2 | 5/2017 | Dmuschewsky et al. |
| 9,655,728 B2 | 5/2017 | Parisi et al. |
| 9,655,729 B2 | 5/2017 | Parisi et al. |
| 9,656,358 B2 | 5/2017 | Charlebois et al. |
| 9,662,214 B2 | 5/2017 | Li et al. |
| 9,668,863 B2 | 6/2017 | Sharp et al. |
| 9,668,871 B2 | 6/2017 | Irwin et al. |
| 9,693,788 B2 | 7/2017 | Metzger |
| 9,693,869 B2 | 7/2017 | Salehi et al. |
| 9,717,598 B2 | 8/2017 | Otto |
| 9,763,794 B2 | 9/2017 | Sanfonietal |
| 9,770,345 B2 | 9/2017 | Belcher et al. |
| 9,788,954 B2 | 10/2017 | Parisi et al. |
| 9,839,522 B2 | 12/2017 | Bechtold et al. |
| 9,918,845 B2 | 3/2018 | Roby et al. |
| 9,931,216 B2 | 4/2018 | Williams et al. |
| 9,937,049 B2 | 4/2018 | Wyss et al. |
| 2002/0082741 A1 | 6/2002 | Mazumder et al. |
| 2002/0198529 A1 | 12/2002 | Masini |
| 2004/0039395 A1 | 2/2004 | Coon et al. |
| 2004/0191106 A1 | 9/2004 | O'Neill et al. |
| 2006/0106388 A1 | 5/2006 | Lococo |
| 2006/0147332 A1 | 7/2006 | Jones et al. |
| 2006/0229715 A1 | 10/2006 | Istephanous |
| 2007/0100461 A1* | 5/2007 | Incavo ............... A61F 2/38 623/20.19 |
| 2007/0142914 A1 | 6/2007 | Jones et al. |
| 2008/0004709 A1* | 1/2008 | O'Neill ............ A61F 2/30942 623/20.35 |
| 2008/0215157 A1 | 9/2008 | Earl et al. |
| 2008/0243258 A1 | 10/2008 | Sancheti |
| 2010/0016980 A1 | 1/2010 | Donno et al. |
| 2010/0016987 A1 | 1/2010 | Scrafton et al. |
| 2010/0318089 A1 | 12/2010 | Metzger et al. |
| 2011/0029093 A1 | 2/2011 | Bojarski et al. |
| 2012/0191204 A1 | 7/2012 | Bae et al. |
| 2012/0239098 A1 | 9/2012 | Bae et al. |
| 2013/0173010 A1 | 7/2013 | Irwin et al. |
| 2013/0218288 A1 | 8/2013 | Fonte et al. |
| 2014/0010951 A1 | 1/2014 | Vargas et al. |
| 2014/0257504 A1 | 9/2014 | Dong et al. |
| 2014/0257507 A1 | 9/2014 | Wang et al. |
| 2014/0277530 A1* | 9/2014 | Stalcup ............ A61B 17/864 623/20.17 |
| 2014/0277540 A1 | 9/2014 | Leszko |
| 2014/0277548 A1 | 9/2014 | Cohen et al. |
| 2014/0316528 A1 | 10/2014 | Bechtold et al. |
| 2014/0371863 A1 | 12/2014 | Vanasse et al. |
| 2015/0032218 A1 | 1/2015 | Landon |
| 2015/0093283 A1 | 4/2015 | Miller et al. |
| 2015/0258735 A1 | 9/2015 | O'Neill et al. |
| 2015/0305754 A1 | 10/2015 | Metzger |
| 2015/0305878 A1 | 10/2015 | O'Neil et al. |
| 2015/0342741 A1 | 12/2015 | Davignon et al. |
| 2015/0342742 A1 | 12/2015 | Ferro et al. |
| 2015/0359638 A1 | 12/2015 | Khowaylo et al. |
| 2016/0015520 A1 | 1/2016 | Smith et al. |
| 2016/0157906 A1 | 6/2016 | Hollis et al. |
| 2016/0157908 A1 | 6/2016 | Cawley et al. |
| 2016/0199193 A1 | 7/2016 | Willis et al. |
| 2016/0213821 A1 | 7/2016 | Melkent et al. |
| 2016/0228255 A1 | 8/2016 | Samuelson et al. |
| 2016/0278929 A1 | 9/2016 | Harris et al. |
| 2016/0296289 A1 | 10/2016 | Choudhury et al. |
| 2016/0310279 A1 | 10/2016 | Samuelson et al. |
| 2016/0310282 A1 | 10/2016 | Bojarski et al. |
| 2017/0014235 A1 | 1/2017 | Jones et al. |
| 2017/0027700 A1 | 2/2017 | Cohen et al. |
| 2017/0035572 A1 | 2/2017 | Servidio |
| 2017/0042576 A1 | 2/2017 | Butters et al. |
| 2017/0056025 A1 | 3/2017 | Trachsler et al. |
| 2017/0071744 A1 | 3/2017 | Bali et al. |
| 2017/0312084 A1 | 11/2017 | Ferro et al. |
| 2018/0049880 A1 | 2/2018 | Sun et al. |
| 2018/0065324 A1 | 3/2018 | Isobe et al. |
| 2018/0161167 A1 | 6/2018 | Bae et al. |
| 2018/0250019 A1 | 9/2018 | Nguyen et al. |
| 2018/0250022 A1 | 9/2018 | Nguyen et al. |
| 2018/0250134 A1 | 9/2018 | Justin et al. |

OTHER PUBLICATIONS

Restrepo et al., Size Controlled Mechanochemical Synthesis of ZrSi2, *The Royal Society of Chemistry*, ChemComm, Aug. 30, 2012 (3 pages).

Bone Ingrowth Performance of OsteoSync Ti, Sites Medical Research and Development, Document: 2007-001-40 REV A (5 pages).

Mechanical Characteristics of OsteoSync Ti, Sites Medical Research and Development, Document: 2007-001-41 REV A (4 pages).

* cited by examiner

ORTHOPEDIC IMPLANTS AND METHODS

RELATED APPLICATIONS

The present application claims the benefit of U.S. Provisional Patent Application Ser. No. 62/694,834, filed Jul. 6, 2018 and entitled ORTHOPEDIC IMPLANTS AND METHODS. The present application is also a continuation-in-part of U.S. patent application Ser. No. 15/622,688, filed Jun. 14, 2017, which claims the benefit of U.S. Provisional Patent Application Ser. No. 62/466,249, filed Mar. 2, 2017 and entitled COMPOSITE JOINT ARTHROPLASTY SYSTEMS AND METHODS. All of the foregoing are incorporated by reference as though set forth herein in their entirety.

TECHNICAL FIELD

The present disclosure relates to surgical systems and methods. More specifically, the present disclosure relates to implants and related methods for joint arthroplasty.

BACKGROUND

Joint arthroplasty procedures are surgical procedures in which one or more articulating surfaces of a joint are replaced with prosthetic articulating surfaces. Such procedures are becoming increasingly commonplace.

For a successful joint arthroplasty, it is important that the joint implants remain in place and maintain the necessary wear characteristics. Further, it is desirable for the arthroplasty procedure to be carried out quickly and smoothly. Many existing arthroplasty implants and methods are time-consuming to implant, do not form a sufficient attachment to the underlying bone, or leave excessive wear debris.

SUMMARY

The various systems and methods of the present disclosure have been developed in response to the present state of the art, and in particular, in response to the problems and needs in the art that have not yet been fully solved by currently available arthroplasty systems and methods. The systems and methods of the present disclosure may provide prostheses that enhance bone fixation, manufacturability, and overall outcomes for arthroplasty procedures.

According to one embodiment, a knee implant may be provided, for replacing a natural articular surface on bone. The knee implant may have a joint facing side with an articular surface shaped to replace the natural articular surface, a bone anchoring side comprising a bone engagement surface, and a bone engagement pad secured to at least part of the bone engagement surface. The articular surface may be one of a natural tibial articular surface and a natural femoral articular surface. The bone engagement pad may have a transverse portion extending transverse to a length of the bone. The transverse portion may have a pad bone-facing surface with a first porosity level, and a pad joint-facing surface on an opposite side of the transverse portion from the pad bone-facing surface. The pad joint-facing surface may have a second porosity level lower than the first porosity level. The bone engagement pad may further have one or more protruding portions extending generally perpendicular to the transverse portion. The bone engagement surface may be formed via a first manufacturing process selected from the group consisting of forging, milling, and casting. The bone engagement pad may be formed via a second manufacturing process different from the first manufacturing process. The second manufacturing process may be an additive manufacturing process.

The bone engagement pad may extend generally transverse to a length of the bone, and may have a thickness, parallel to the length, that is substantially uniform. The thickness may be within the range of 0.5 mm to 1.5 mm.

The bone engagement surface may have a bone engagement feature extending through an aperture formed in the transverse portion. The one or more protruding portions may extend from one or more edges of the aperture, alongside one or more surfaces of the bone engagement feature.

According to one embodiment, a prosthesis for replacing a natural articular surface on bone may have a joint facing side with an articular surface, a bone anchoring side with a bone engagement surface, and a bone engagement pad secured to at least part of the bone engagement surface. The bone engagement pad may have a pad bone-facing surface with a first porosity level, and a pad joint-facing surface with a second porosity level lower than the first porosity level.

The bone engagement surface may be formed via a first manufacturing process. The bone engagement pad may be formed via a second manufacturing process different from the first manufacturing process.

The first manufacturing process may be selected from the group consisting of forging, milling, and casting. The second manufacturing process may be an additive manufacturing process.

The bone engagement pad may have a thickness within the range of 0.5 mm to 1.5 mm.

The bone engagement pad may have a transverse portion that extends generally transverse to a length of the bone. The pad bone-facing surface and the pad joint-facing surface may be on opposite sides of the bone engagement pad. The transverse portion may have a thickness, parallel to the length, that is substantially uniform.

The bone engagement pad may have a transverse portion extending transverse to a length of the bone. The pad bone-facing surface and the pad joint-facing surface may be on opposite sides of the transverse portion. The bone engagement pad may further have one or more protruding portions extending generally perpendicular to the transverse portion.

The bone engagement surface may have a bone engagement feature extending through an aperture formed in the transverse portion. The one or more protruding portions may extend from one or more edges of the aperture, alongside one or more surfaces of the bone engagement feature.

The bone engagement pad may have a transverse portion that extends generally transverse to a length of the bone. The pad bone-facing surface and the pad joint-facing surface may be on opposite sides of the bone engagement pad. The transverse portion may have a porosity gradient by which porosity of the transverse portion gradually increases toward the pad bone-facing surface.

The bone engagement pad may have a transverse portion that extends generally transverse to a length of the bone. The pad bone-facing surface and the pad joint-facing surface may be on opposite sides of the bone engagement pad. The transverse portion may have a low-porosity layer proximate the pad joint-facing surface, by which a porosity of the transverse portion abruptly increases toward the pad bone-facing surface.

The prosthesis may be a knee implant. The articular surface may be shaped to replace the natural articular surface. The natural articular surface may be one of a natural tibial surface and a natural femoral articular surface.

According to one embodiment, a prosthesis for replacing a natural articular surface on bone may have a joint facing side with the articular surface, a bone anchoring side with a bone engagement surface, and a bone engagement pad secured to at least part of the bone engagement surface. The bone engagement pad may have a transverse portion extending transverse to a length of the bone, and one or more protruding portions extending generally perpendicular to the transverse portion.

The bone engagement surface may be formed via a first manufacturing process, and the bone engagement pad may be formed via a second manufacturing process different from the first manufacturing process.

The first manufacturing process may be selected from the group consisting of forging, milling, and casting. The second manufacturing process may be an additive manufacturing process.

The bone engagement pad may have a thickness within the range of 0.5 mm to 1.5 mm.

The transverse portion may extend generally transverse to a length of the bone, and may have a thickness, parallel to the length, that is substantially uniform.

The bone engagement surface may have a bone engagement feature extending through an aperture formed in the transverse portion. The one or more protruding portions may extend from one or more edges of the aperture, alongside one or more surfaces of the bone engagement feature.

The prosthesis may be a knee implant. The articular surface may be shaped to replace the natural articular surface. The natural articular surface may be one of a natural tibial surface and a natural femoral articular surface.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 10, is not intended to limit the scope of the claims, as claimed, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
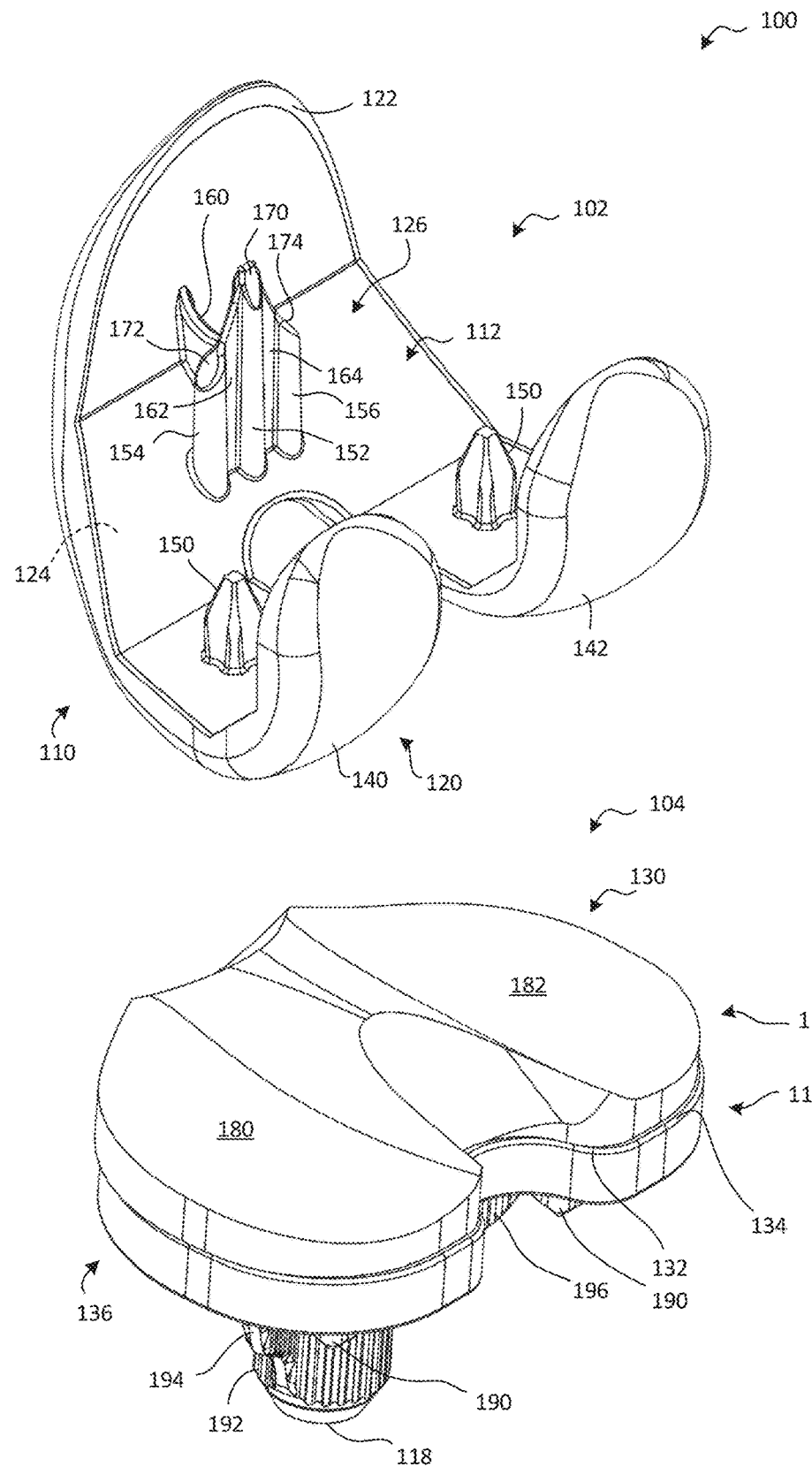
FIG. 1 is a perspective view of a knee arthroplasty system according to one embodiment.
Figure 2A:
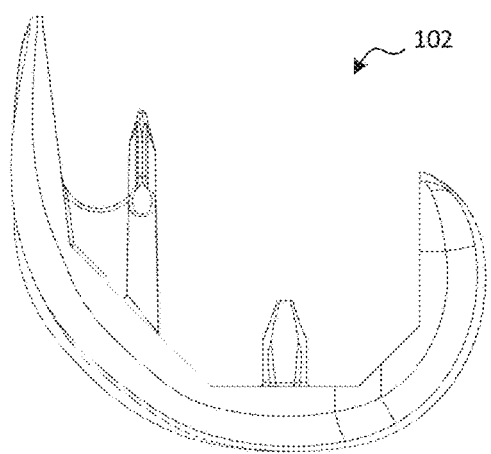
FIGS. 2A through 2F are left, posterior, right, anterior, cephalad, and caudal views, respectively, of the femoral prosthesis of the knee arthroplasty system of FIG. 1.
Figure 2B:
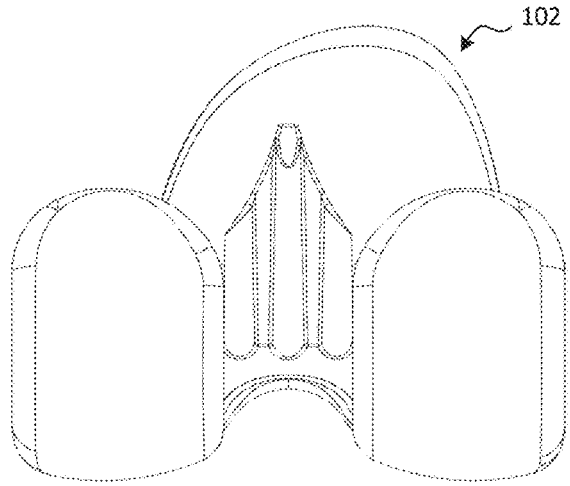
Figure 2C:
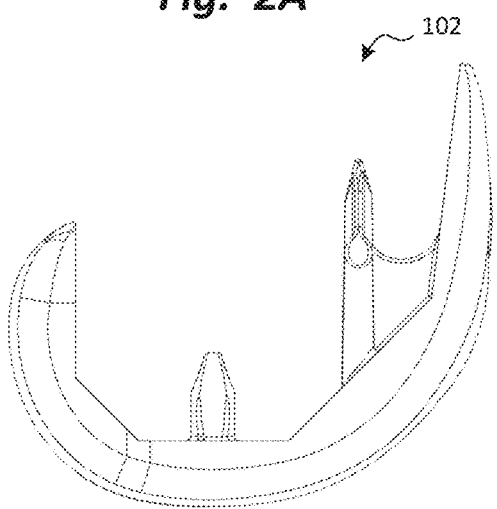
Figure 2D:
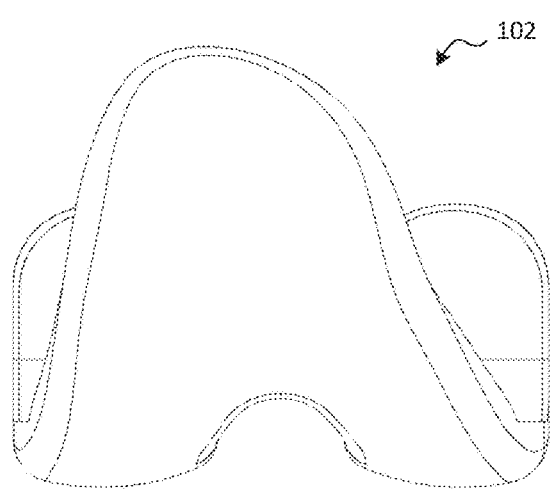
Figure 2E:
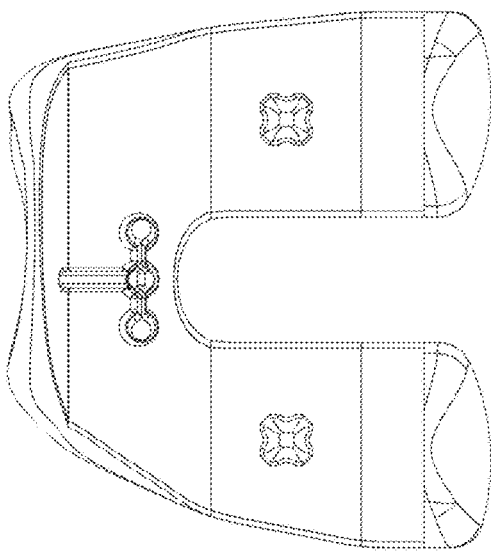
Figure 2F:
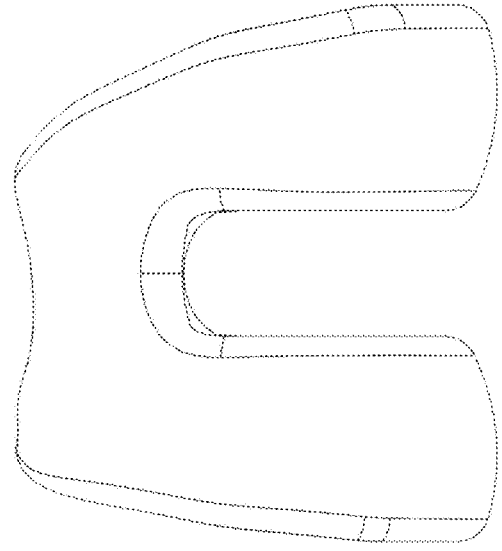

FIG. 1 is a perspective view of a knee arthroplasty system, or system 100, according to one embodiment. The system 100 may be designed to replace the natural articulating surfaces of a knee joint, and may thus have a femoral prosthesis 102 and a tibial prosthesis 104. In some embodiments, the system 100 may be designed to replace only the femoral or tibial articulating surfaces, and may thus include only the femoral prosthesis 102 or the tibial prosthesis 104.

The femoral prosthesis 102 and the tibial prosthesis 104 may each have an articulating component with replacement articulating surfaces, and a bone anchoring component secured to the articulating component to secure the articulating component to the underlying bone. Specifically, the femoral prosthesis 102 may have a femoral articulating component 110 and a femoral bone anchoring component 112. Similarly, the tibial prosthesis 104 may have a tibial articulating component 114 and a tibial bone anchoring component 116. The tibial prosthesis 104 may also have a tibial fastener 118.

Each of the aforementioned articulating components and bone anchoring components may have a joint-facing side and a bone-facing side. Thus, the femoral articulating component 110 may have a joint-facing side 120 and a bone-facing side 122, and the femoral bone anchoring component 112 may have a joint-facing side 124 and a bone-facing side 126. Similarly, the tibial articulating component 114 may have a joint-facing side 130 and a bone-facing side 132, and the tibial bone anchoring component 116 may have a joint-facing side 134 and a bone-facing side 136.

The bone-facing side 122 of the femoral articulating component 110 may have a shape that matches the shape of the joint-facing side 124 of the femoral bone anchoring component 112, and may be secured to the joint-facing side 124 of the femoral bone anchoring component 112 in a manner that will be set forth in greater detail subsequently. Similarly, the bone-facing side 132 of the tibial articulating component 114 may have a shape that matches the shape of the joint-facing side 134 of the tibial bone anchoring component 116, and may be secured to the joint-facing side 134 of the tibial bone anchoring component 116 in a manner that will be set forth in greater detail subsequently.

The joint-facing side 120 of the femoral articulating component 110 may have a first articulating surface 140 and a second articulating surface 142, which are shaped to mimic the shapes of the natural articulating surfaces on the end of the femur. The shapes depicted in FIG. 1 are merely exemplary; according to alternative embodiments, any articulating surface shape known in the art may be used.

The bone-facing side 126 of the femoral bone anchoring component 112 may have a plurality of features that enhance engagement of the femoral bone anchoring component 112 with the underlying bone. For example, the bone-facing side 126 of the femoral bone anchoring component 112 may have a pair of posts 150, a first femoral anchoring member 152, a second femoral anchoring member 154, and a third femoral anchoring member 156, which protrude from various surfaces of the bone-facing side 126 of the femoral bone anchoring component 112, as will be set forth in greater detail subsequently.

The first femoral anchoring member 152, the second femoral anchoring member 154, and the third femoral anchoring member 156 may be connected to each other and to the remainder of the bone-facing side 126 by a primary femoral web 160, a first femoral web 162, and a second femoral web 164. Specifically, the second femoral anchoring member 154 may be connected to the first femoral anchoring member 152 with the first femoral web 162, and the third femoral anchoring member 156 may be connected to the first femoral anchoring member 152 with the second femoral web 164. The first femoral anchoring member 152 may have a tip 170 with a tapered shape. The first femoral anchoring member 152, the first femoral web 162, and the second femoral anchoring member 154 may cooperate to define a first bevel 172. Similarly, the first femoral anchoring member 152, the second femoral web 164, and the third femoral anchoring member 156 may cooperate to define a second bevel 174.

The joint-facing side 130 of the tibial articulating component 114 may also have a first articulating surface 180 and a second articulating surface 182. After implantation of the femoral prosthesis 102 and the tibial prosthesis 104, the first articulating surface 140 may articulate with the first articulating surface 180, and the second articulating surface 142 may articulate with the second articulating surface 182. The articulation of the femoral articulating component 110 with the tibial articulating component 114 may be designed to mimic that of the natural knee joint.

The bone-facing side 136 of the tibial bone anchoring component 116 may have a plurality of posts 190 that protrude into the bone from the remainder of the bone-facing side 136. Further, the bone-facing side 136 of the tibial bone anchoring component 116 may have a central post 192 that also protrudes from the remainder of the bone-facing side 136. The central post 192 may further be connected to the remainder of the bone-facing side 136 by a first tibial web 194 and a second tibial web 196.

FIGS. 2A through 2F are left, posterior, right, anterior, cephalad, and caudal views, respectively, of the femoral prosthesis 102 of the system 100 of FIG. 1. These views further depict the various features described in connection with FIG. 1.

Figure 3:
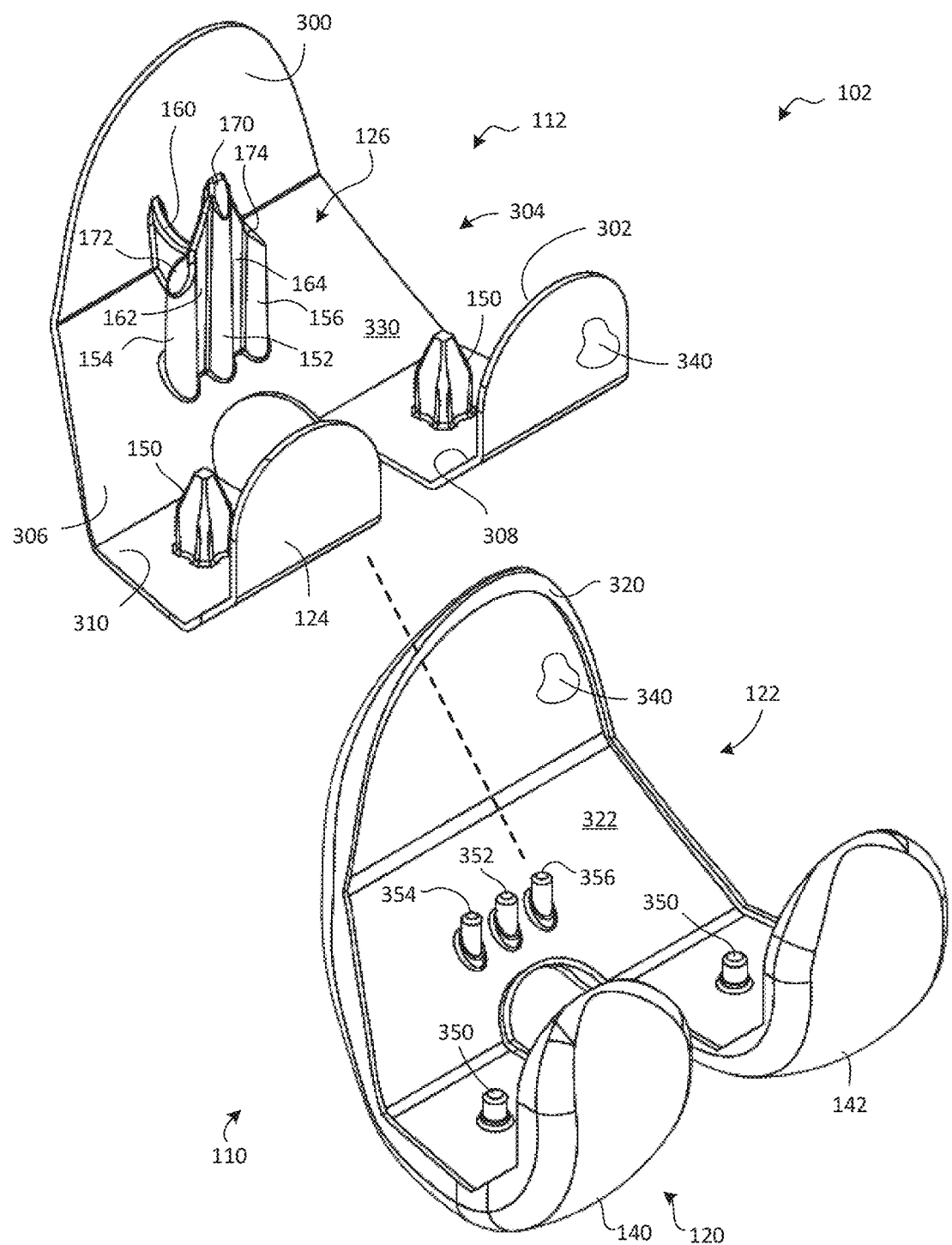
FIG. 3 is an exploded, perspective view of the femoral prosthesis of the knee arthroplasty system of FIG. 1.

FIG. 3 is an exploded, perspective view of the femoral prosthesis 102 of the system 100 of FIG. 1. The femoral articulating component 110 and the femoral bone anchoring component 112 may optionally be manufactured separately from each other. Accordingly, different manufacturing processes may be used to form the femoral articulating component 110 and the femoral bone anchoring component 112. This may advantageously enable the use of materials and/or processes for each of the femoral articulating component 110 and the femoral bone anchoring component 112 that are best suited for the role to be performed.

For example, the femoral articulating component 110 may be designed to endure cyclical loading in friction and compression. Accordingly, high-strength and/or low-wear materials and surface properties may be desired. Accordingly, the femoral articulating component 110 may be made of a relatively hard material such as an alloy of Cobalt Chromium ("Cobalt Chrome,"). Specifically, the femoral articulating component 110 may be made of an alloy of Cobalt Chromium Molybdenum (CoCrMo). A manufacturing process such as casting may be used. In some embodiments, the first articulating surface 140 and the second articulating surface 142 may be specially processed in a manner that increases their hardness and/or wear resistance.

Conversely, the femoral bone anchoring component 112 may be designed to provide high-strength fixation of the femoral articulating component 110 to the underlying bone. It may be desirable for the femoral bone anchoring component 112 to have a porous structure that encourages bone in-growth. Accordingly, the femoral bone anchoring component 112 may be formed of a metal such as Titanium, or specifically, direct metal laser sintered ("DMLS") Titanium. The femoral bone anchoring component 112 may be formed via an additive manufacturing method such as 3D printing. Such manufacturing methods may facilitate the creation of a porous structure, particularly on the bone-facing side 126 of the femoral bone anchoring component 112.

In some embodiments, the femoral bone anchoring component 112 may be made such that the porosity varies in a gradient through the thickness of the femoral bone anchoring component 112. Thus, the bone-facing side 126 of the femoral bone anchoring component 112 may be made more porous to facilitate bone in-growth, while the joint-facing side 124 of the femoral bone anchoring component 112 may be made less porous to enhance attachment of the joint-facing side 124 to the bone-facing side 122 of the femoral articulating component 110. In some embodiments, the joint-facing side 124 may be made substantially solid (i.e., nonporous) to enhance adhesion to the bone-facing side 122 of the femoral articulating component 110, while the bone-facing side 126 may be highly porous.

As shown, the bone-facing side 122 of the femoral articulating component 110 may have an anterior portion 300, a posterior portion 302, and a distal portion 304. Upon implantation of the femoral articulating component 110, the anterior portion 300 may be located on the anterior side of the knee, the posterior portion 302 may be located on the posterior side of the knee, and the distal portion 304 may be located at the distal end of the femur. The distal portion 304 may be divided into three faces: an anterior-distal face 306, a posterior-distal face 308, and a distal face 310. The anterior-distal face 306 may reside between the anterior portion 300 and the distal face 310, and the posterior-distal face 308 may be reside between the posterior portion 302 and the distal face 310.

As shown, the posts 150 may protrude from the distal face 310. The first femoral anchoring member 152, the second femoral anchoring member 154, and the third femoral anchoring member 156 may protrude from the posterior-distal face 308. The primary femoral web 160 may connect the first femoral anchoring member 152 to the anterior portion 300. The first femoral web 162 may connect the first femoral anchoring member 152 to the second femoral anchoring member 154 and to the anterior-distal face 306. Similarly, the second femoral web 164 may connect the first femoral anchoring member 152 to the third femoral anchoring member 156 and the anterior-distal face 306.

The first femoral anchoring member 152, the second femoral anchoring member 154, the third femoral anchoring member 156, the primary femoral web 160, the first femoral web 162, and the second femoral web 164 may cooperate to enhance engagement of the bone-facing side 126 of the femoral bone anchoring component 112 with the underlying bone. Specifically, these features may add to the surface area of the bone-facing side 126 in contact with the bone, providing a stronger bond with the bone via bone in-growth and/or application of bone cement. The position of these features on the anterior-distal face 306, proximate the anterior portion 300 may enable them to penetrate a relatively dense, sturdy bone mass proximate the distal end of the femur. Specifically, the bone that underlies the natural femoral articular surfaces to be replaced may, due to mechanical loading, have a denser structure and/or a thicker layer of cortical bone. Accordingly, the first femoral anchoring member 152, the second femoral anchoring member 154, the third femoral anchoring member 156, the primary femoral web 160, the first femoral web 162, and the second femoral web 164 may be optimally positioned for anchorage in strong, relatively dense bone that is likely to provide solid anchorage for the femoral bone anchoring component 112.

The posts 150, the first femoral anchoring member 152, the second femoral anchoring member 154, the third femoral anchoring member 156, the primary femoral web 160, the first femoral web 162, and the second femoral web 164 may all protrude in a cephalad direction so that these features can penetrate the bone, helping to anchor the femoral articulating component 110 on the distal end of the femur (not shown). These features may also be shaped to facilitate entry into and/or compaction of the bone.

Specifically, the tip 170, the first bevel 172, and the second bevel 174 may help to spread bone out of the path of the first femoral anchoring member 152, the second femoral anchoring member 154, the third femoral anchoring member 156, the first femoral web 162, and the second femoral web 164 as these features are pressed into the bone, thereby easing placement of the femoral prosthesis 102 on the distal end of the femur. Further, due to the presence of the tip 170, the first bevel 172, and/or the second bevel 174, the bone surrounding these features in their implanted state may be compacted and/or strengthened.

As also shown in FIG. 3, the bone-facing side 122 of the femoral articulating component 110 may have a peripheral ridge 320 that defines an interior recess 322. The shape of the interior recess 322 may closely match that of the joint-facing side 124 of the femoral bone anchoring component 112 so that the joint-facing side 124 of the femoral bone anchoring component 112 can be secured to the interior recess 322. When the femoral bone anchoring component 112 and the femoral articulating component 110 are assembled together, the bone-facing side 126 of the femoral bone anchoring component 112 may lie substantially flush with the peripheral ridge 320 of the bone-facing side 122 of the femoral articulating component 110.

In some embodiments, the bone-facing side 126 of the femoral bone anchoring component 112 may be treated to enhance porosity and/or bone in-growth. In some examples, the bone-facing side 126 of the femoral bone anchoring component 112 may be processed via a process such as anodizing to form Titanium Dioxide nanotubes on the bone-facing side 126. Specifically, the bone-facing side 126 may be anodized in a Fluoride electrolyte, as set forth in U.S. application Ser. No. 11/913,062, filed Jun. 10, 2008 and entitled "Compositions Comprising Nanostructures for Cell, Tissue and Artificial Organ Growth, and Methods for Making and Using Same, now U.S. Pat. No. 8,414,908, which is incorporated by reference as though set forth herein in its entirety. The result may be the formation of a surface layer 330 of Titanium Dioxide nanotubes on the bone-facing side 126.

The femoral articulating component 110 and the femoral bone anchoring component 112 may be secured together in a variety of ways. Such ways may include, but are not limited to, welding, brazing, press fitting, and the like. According to some embodiments, a substance 340 may be applied to one or both of the surfaces to be secured together via chemical and/or adhesive bonding. Any of the methods mentioned above may be used to secure the tibial articulating component 114 to the tibial bone anchoring component 116.

In addition to or in the alternative to the foregoing attachment methods, the methods disclosed in U.S. application Ser. No. 10/455,846, filed Jun. 6, 2003 and entitled "METHOD FOR ATTACHING A POROUS METAL LAYER TO A METAL SUBSTRATE," now U.S. Pat. No. 6,945,448, may be used. This application is incorporated as though set forth herein in its entirety.

Optionally, the surfaces to be bonded together may have features that facilitate and/or enhance the results of the bonding process. For example, the bone-facing side 122 of the femoral articulating component 110 may have features that cooperate with corresponding features (shown in FIG. 4) on the joint-facing side 124 of the femoral bone anchoring component 112 to help align the femoral articulating component 110 with the femoral bone anchoring component 112 and/or add mechanical fastening to the bonding described above. These features of the bone-facing side 122 may include a pair of post bosses 350, a first femoral anchoring member boss 352, a second femoral anchoring member boss 354, and a third femoral anchoring member boss 356.

Figure 4:
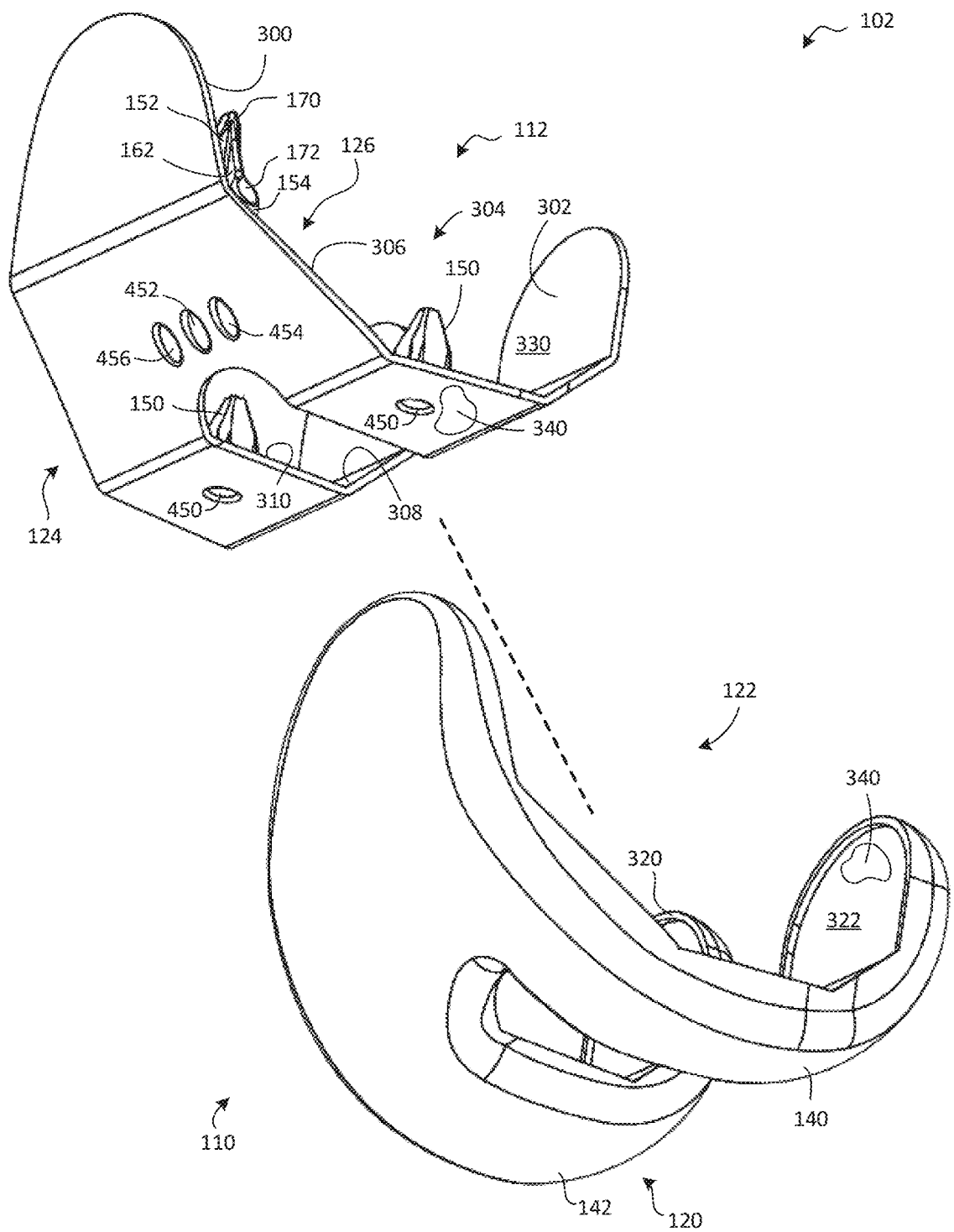
FIG. 4 is an exploded, perspective view, from a different viewpoint, of the femoral prosthesis of the knee arthroplasty system of FIG. 1.
Figure 5A:
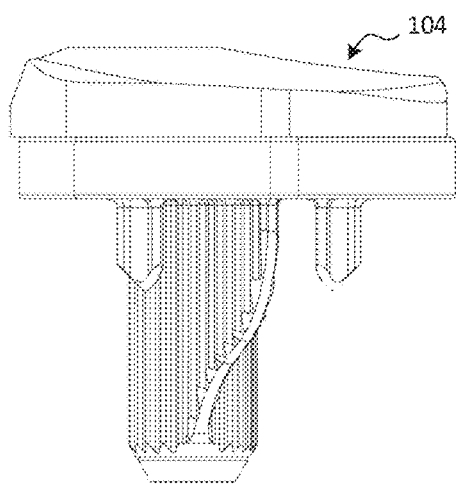
FIGS. 5A through 5F are left, posterior, right, anterior, cephalad, and caudal views, respectively, of the tibial prosthesis of the knee arthroplasty system of FIG. 1.
Figure 5B:
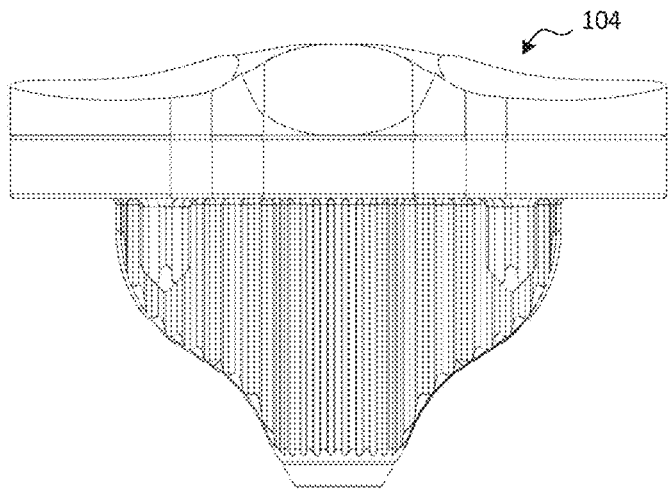
Figure 5C:
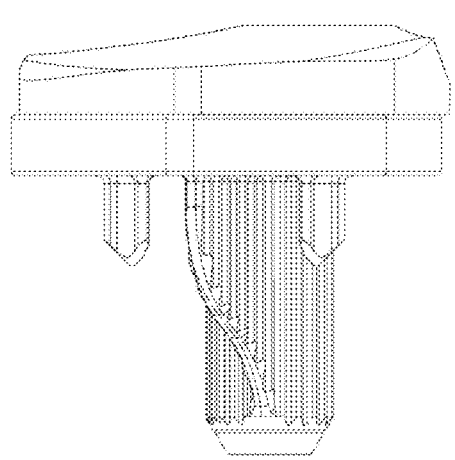
Figure 5D:
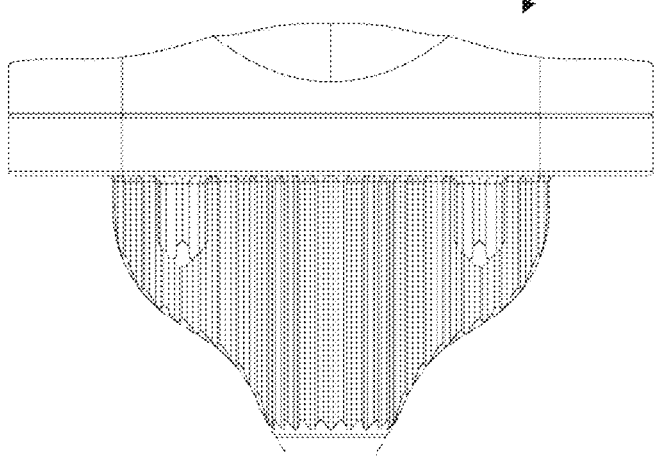
Figure 5E:
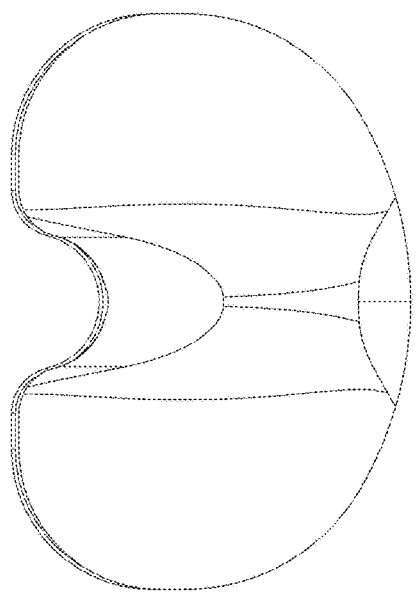
Figure 5F:
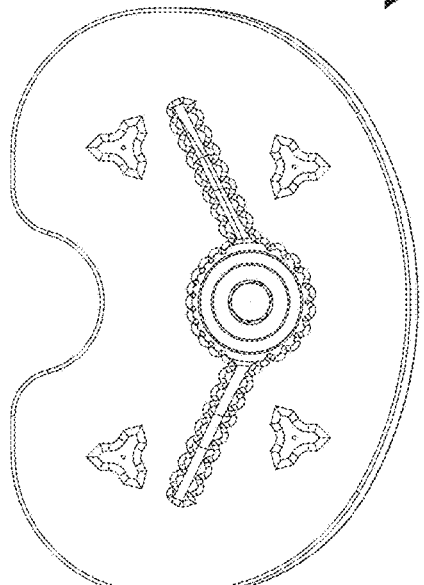

FIG. 4 is an exploded, perspective view, from a different viewpoint, of the femoral prosthesis 102 of the system 100 of FIG. 1. The joint-facing side 124 of the femoral bone anchoring component 112 and the joint-facing side 120 of the femoral articulating component 110 are more clearly visible.

As shown, the joint-facing side 124 of the femoral bone anchoring component 112 may have features that cooperate with the post bosses 350, the first femoral anchoring member boss 352, the second femoral anchoring member boss 354, and the third femoral anchoring member boss 356 of the bone-facing side 122 of the femoral articulating component 110 depicted in FIG. 3. These features may include post bores 450, a first femoral anchoring member bore 452, a second femoral anchoring member bore 454, and a third femoral anchoring member bore 456. Each of the post bores 450 may reside in the interior of one of the posts 150.

Similarly, the first femoral anchoring member bore 452, the second femoral anchoring member bore 454, and the third femoral anchoring member bore 456 may reside in the interiors of the first femoral anchoring member 152, the second femoral anchoring member 154, and the third femoral anchoring member 156, respectively.

The post bores 450 may be shaped to receive the post bosses 350. Similarly, the first femoral anchoring member bore 452, the second femoral anchoring member bore 454, and the third femoral anchoring member bore 456 may be shaped to receive the first femoral anchoring member boss 352, the second femoral anchoring member boss 354, and the third femoral anchoring member boss 356, respectively. If desired, the post bosses 350, the first femoral anchoring member boss 352, the second femoral anchoring member boss 354, and/or the third femoral anchoring member boss 356 may each be tapered to facilitate insertion into the post bores 450, the first femoral anchoring member bore 452, the second femoral anchoring member bore 454, and/or the third femoral anchoring member bore 456, respectively.

The features of the bone-facing side 122 may be received by these features of the joint-facing side 124 with some interference, which may cooperate with the bond described above to enhance attachment of the bone-facing side 122 to the joint-facing side 124. When the femoral articulating component 110 and the femoral bone anchoring component 112 are compressed together, as set forth above, the compression may be sufficient to urge the post bosses 350, the first femoral anchoring member boss 352, the second femoral anchoring member boss 354, and the third femoral anchoring member boss 356 into the post bores 450, the first femoral anchoring member bore 452, the second femoral anchoring member bore 454, and the third femoral anchoring member bore 456, respectively.

Additionally or alternatively, heat applied to the femoral articulating component 110 and/or the femoral bone anchoring component 112 may cause thermal expansion that eases insertion of the post bosses 350, the first femoral anchoring member boss 352, the second femoral anchoring member boss 354, and the third femoral anchoring member boss 356 into the post bores 450, the first femoral anchoring member bore 452, the second femoral anchoring member bore 454, and the third femoral anchoring member bore 456, respectively. The femoral articulating component 110 may be made such that the femoral articulating component 110 has higher thermal expansion than the femoral bone anchoring component 112. Thus, after insertion of the bosses into the bores, the femoral articulating component 110 and the femoral bone anchoring component 112 may be cooled, allowing the bores to tighten around the bosses.

In alternative embodiments, other positive and/or negative features may be used. Further, if desired, the positive features may be on the joint-facing side 124 of the femoral bone anchoring component 112, and the negative features may be on the bone-facing side 122 of the femoral articulating component 110.

FIGS. 5A through 5F are left, posterior, right, anterior, cephalad, and caudal views, respectively, of the tibial prosthesis 104 of the system 100 of FIG. 1. These views further depict the various features described in connection with FIG. 1.

Figure 6:
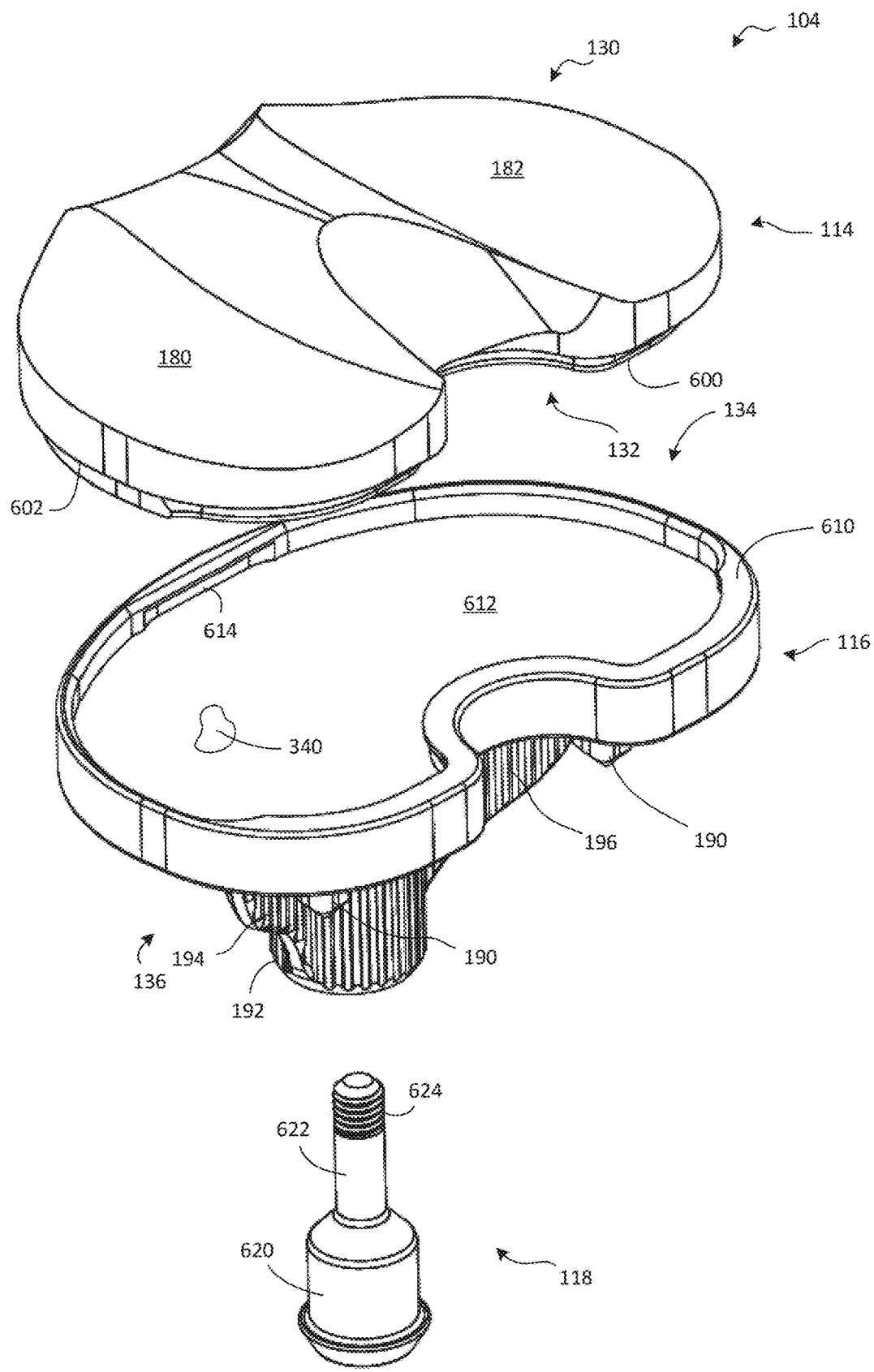
FIG. 6 is an exploded, perspective view of the tibial prosthesis of the knee arthroplasty system of FIG. 1.

FIG. 6 is an exploded, perspective view of the tibial prosthesis 104 of the system 100 of FIG. 1. As with the femoral prosthesis 102, the tibial articulating component 114 and the tibial bone anchoring component 116 may optionally be manufactured separately from each other. Accordingly, different manufacturing processes may be used to form the tibial articulating component 114 and the tibial bone anchoring component 116. For example, the tibial articulating component 114 may be formed via casting, and the tibial bone anchoring component 116 may be formed via additive manufacturing such as 3D printing.

Like the femoral articulating component 110, the tibial articulating component 114 may be made of Cobalt Chromium, or Cobalt Chromium Molybdenum. Similarly, like the femoral bone anchoring component 112, the tibial bone anchoring component 116 may be made of DMLS Titanium. A gradient of porosities may be present in the tibial bone anchoring component 116, with greater porosity on the bone-facing side 136, and lesser porosity on the joint-facing side 134. If desired, the joint-facing side 134 may be made substantially nonporous to enhance adhesion to the tibial articulating component 114, and the bone-facing side 136 may have a high level of porosity to promote bone ingrowth.

As shown, the bone-facing side 132 of the tibial articulating component 114 may have a central plateau 600 that extends toward the tibial bone anchoring component 116, and a peripheral recess 602 that encircles the central plateau 600 and is recessed from the tibial bone anchoring component 116. The joint-facing side 134 of the tibial bone anchoring component 116 may have a shape that is complementary to that of the bone-facing side 132 of the tibial articulating component 114. Specifically, the joint-facing side 134 may have a peripheral ridge 610 that encircles an interior recess 612. An alcove 614 may extend into the peripheral ridge 610, from the space above the interior recess 612. When the tibial articulating component 114 and the tibial bone anchoring component 116 are assembled together, the central plateau 600 may be received within the interior recess 612, and the peripheral ridge 610 may engage the central plateau 600.

In some embodiments, the tibial articulating component 114 and the tibial bone anchoring component 116 may be secured together by the same bonding process described above in connection with the femoral articulating component 110 and the femoral bone anchoring component 112 of the femoral prosthesis 102, or with a modified version of such a bonding process. Thus, FIG. 6 depicts the exemplary application of the substance 340, which may be a paste or the like, to the interior recess 612 of the joint-facing side 134 of the tibial bone anchoring component 116.

FIG. 6 also depicts the tibial fastener 118 in greater detail. The tibial fastener 118 may have an enlarged head 620 and a shank 622 with threads 624 thereon that enable the tibial fastener 118 to threadably engage the tibial bone anchoring component 116, as will be discussed in greater detail subsequently.

Figure 7:
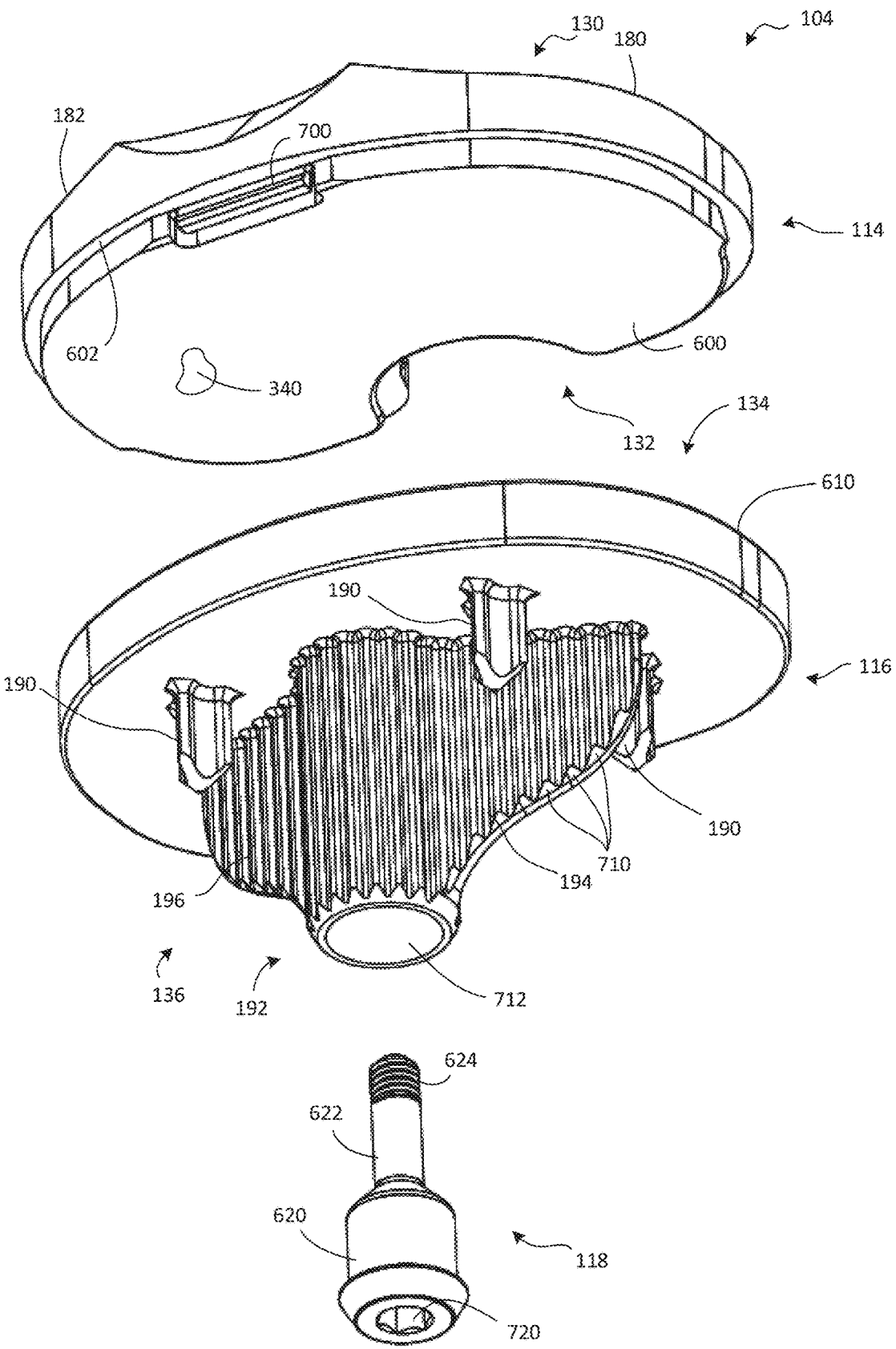
FIG. 7 is an exploded, perspective view, from a different viewpoint, of the tibial prosthesis of the knee arthroplasty system of FIG. 1.

FIG. 7 is an exploded, perspective view, from a different viewpoint, of the tibial prosthesis 104 of the system 100 of FIG. 1. As shown, the central plateau 600 of the bone-facing side 132 of the tibial articulating component 114 may have a lip 700 that protrudes anteriorly. When the tibial articulating component 114 and the tibial bone anchoring component 116 are assembled, the lip 700 may protrude into the alcove 614 depicted in FIG. 6. Engagement of the lip 700 and the alcove 614 may further help to hold the anterior portions of the tibial articulating component 114 and the tibial bone anchoring component 116 together.

FIG. 7 also depicts the bone-facing side 136 of the tibial bone anchoring component 116 in greater detail. Four of the posts 190 may be present on the bone-facing side 136, and may help enhance the level of engagement of the bone-facing side 136 with the underlying bone, and in particular, with the cortical bone at the proximal end of the tibia. The central post 192, the first tibial web 194, and the second tibial web 196 may each extend distally from the remainder of the bone-facing side 136, and may cooperate to provide a greater surface area in engagement with the underlying bone. Thus, the central post 192, the first tibial web 194, and the second tibial web 196 may As shown, the central post 192, the first tibial web 194, and the second tibial web 196 may each have a crenellated shape, with crenellations 710 shown in FIG. 7. The crenellations 710 may further increase the surface area of the bone-facing side 136 in contact with the bone of the tibia, thereby further enhancing the potential for bone cement bonding and/or bone in-growth between the tibia and the bone-facing side 136. Further, if desired, the tibial bone anchoring component 116 may be processed as described above in the description of the femoral bone anchoring component 112, such that the tibial bone anchoring component 116 has a surface layer 330 formed of Titanium Dioxide nanotubes. Such a surface layer 330 may further enhance bone in-growth to further secure the bone-facing side 136 to the bone of the tibia.

As mentioned previously, the tibial articulating component 114 and the tibial bone anchoring component 116 may be secured together through the use of any of a variety of methods. Some of these are mentioned above in the description of assembly of the femoral articulating component 110 and the femoral bone anchoring component 112. Again, a substance 340 may optionally be applied to the bone-facing side 132 of the tibial articulating component 114 and/or to the joint-facing side 134 of the tibial bone anchoring component 116 to facilitate attachment via chemical and/or adhesive bonding.

As further shown in FIG. 7, the central post 192 may have a bore 712 that receives the tibial fastener 118. The bore 712 may have interior threads (not shown) that receive the threads 624 of the shank 622 of the tibial fastener 118. The tibial fastener 118 may serve to seal the bore 712 and reduce the chance of having toxins or microbes enter the bore 712 during implantation. The enlarged head 620 of the tibial fastener 118 may have a socket 720 with a hexagonal or other shape that can receive the shaped distal end of a removal tool (not shown), such as a hex key, to facilitate rotation of the tibial fastener 118 to remove the tibial fastener 118 from the bore 712.

Figures 8A, 8B:
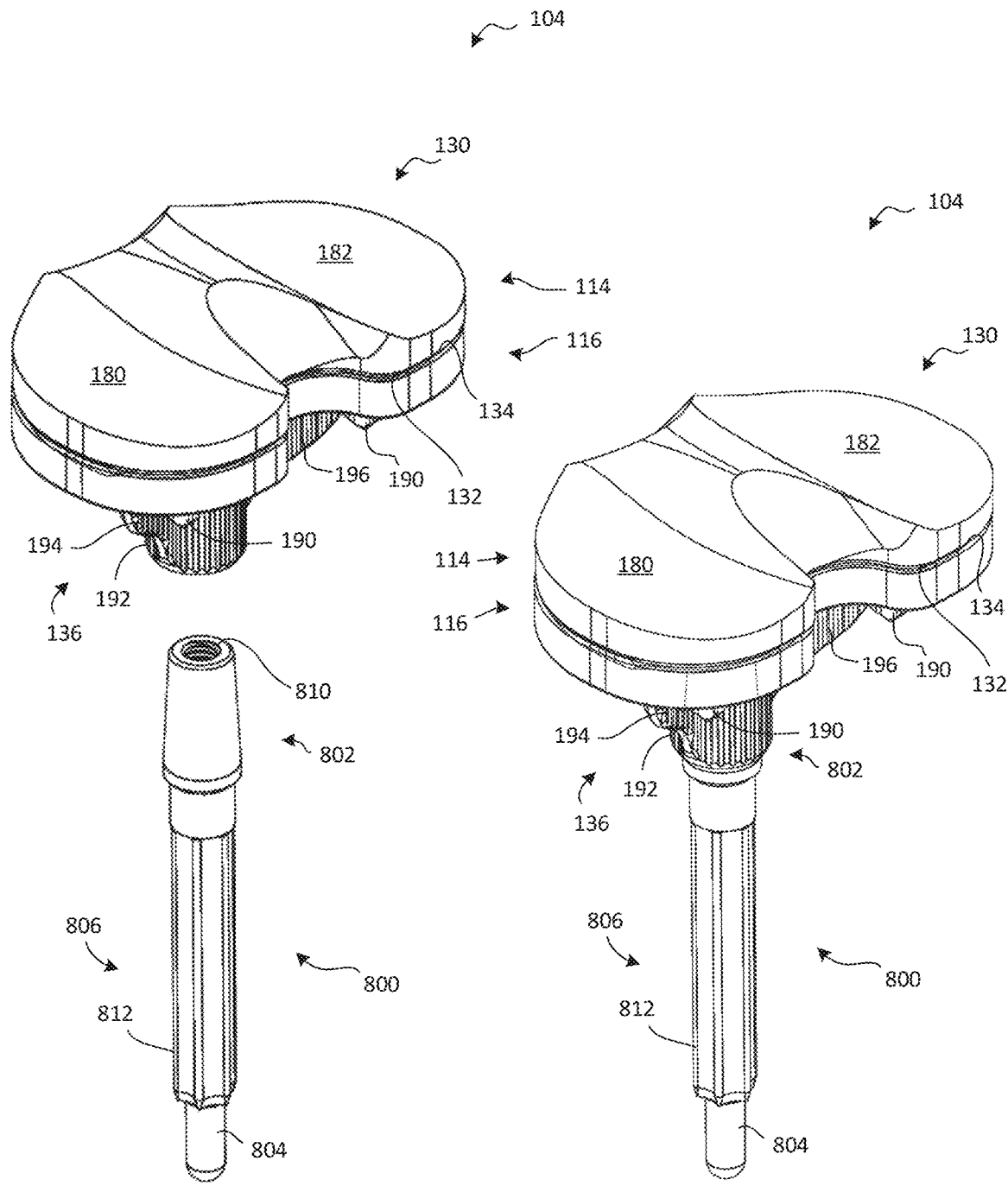
FIGS. 8A and 8B are exploded and fully-assembled perspective views, respectively, of the tibial prosthesis of FIG. 1, with an optional keel.

FIGS. 8A and 8B are exploded and fully-assembled perspective views, respectively, of the tibial prosthesis 104 of FIG. 1, with an optional anchoring member in the form of a keel 800. The keel 800 may have a proximal end 802 and a distal end 804, with a shank 806 extending between the proximal end 802 and the distal end 804. The proximal end 802 may be shaped to be inserted into the bore 712 of the central post 192 of the tibial bone anchoring component 116 of the tibial prosthesis 104, as shown in FIG. 8B.

Specifically, the proximal end 802 may have a generally frustoconical shape. The walls of the bore 712 may define a similar, complementary shape. If desired, the proximal end 802 may be press-fitted into the bore 712. Additionally or alternatively, the proximal end 802 may have threads 810, which may engage corresponding threads (not shown) within the bore 712. In the alternative, the threads 810 may be used to receive another fastener (not shown), which may, in turn, be secured within the bore 712.

The tibial prosthesis 104 may be provided to the surgeon with the tibial fastener 118 in place within the bore 712. The surgeon may remove the tibial fastener 118 from the bore 712, and may insert and secure the proximal end 802 of the keel 800 within the bore 712. The intramedullary space of the tibia may be reamed and/or otherwise prepared to receive the keel 800 prior to attachment of the tibial prosthesis 104, with the keel 800, to the tibia.

The keel 800 may help provide additional bone engagement and/or rotational stability for the tibial prosthesis 104. Thus, the shank 806 may optionally have a plurality of splines 812 that protrude outward from the axis of the shank 806 to engage the surrounding bone. The splines 812 may increase the surface area of the keel 800 in contact with the bone to increase bone engagement, and may further resist rotation of the keel 800 within the bone. If desired, some or all of the keel 800 may have a porous structure that facilitates bone in-growth and/or bone cement engagement. Additionally or alternatively, the keel 800 may be anodized to form a surface layer 330, as set forth in connection with the femoral bone anchoring component 112 and the tibial bone anchoring component 116.

Figure 9:
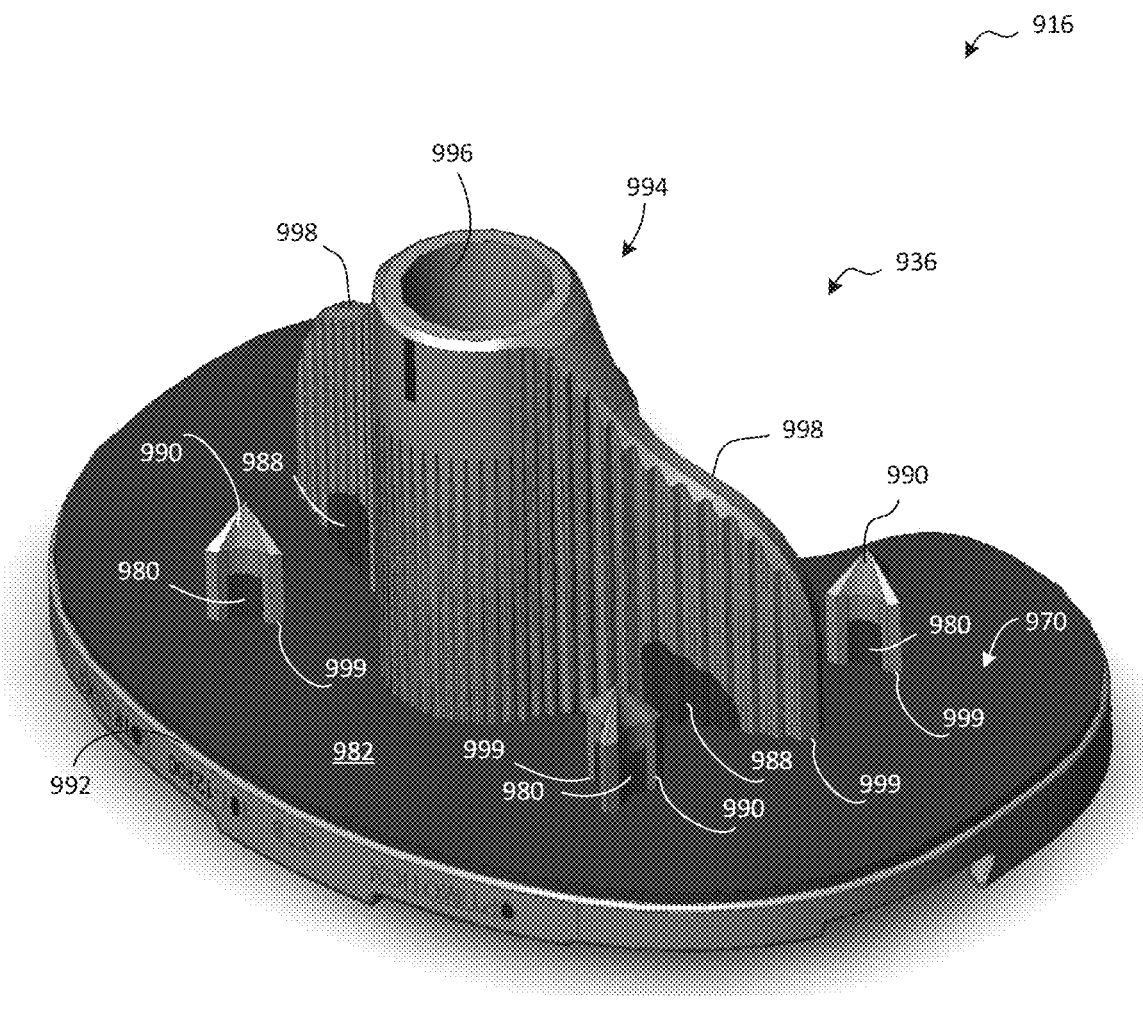
FIG. 9 is a perspective view of a tibial bone anchoring component of a tibial prosthesis of a system according to one alternative embodiment.

FIG. 9 is a perspective view of a tibial bone anchoring component 916 of a tibial prosthesis of a system according to one alternative embodiment. The tibial bone anchoring component 916 may have a joint-facing side 134 and a bone-facing side 936. The joint-facing side 934 may be identical or similar to the joint-facing side 134 of the tibial bone anchoring component 116 of FIGS. 1 through 5. Like the tibial bone anchoring component 116 of FIGS. 1 through 5, the tibial bone anchoring component 916 of FIG. 9 may be designed to be secured to an articulating component like the tibial articulating component 114 of FIGS. 1 through 5. In the alternative, the tibial bone anchoring component 916 may be designed as a standalone tibial implant, with bone apposition surfaces and articulating surfaces, such as the first articulating surface 180 and the second articulating surface 182 of the tibial articulating component 114, which may be formed directly on the superior surface (not shown) of the tibial bone anchoring component 916, if desired.

Like the bone-facing side 136 of the tibial bone anchoring component 116, the bone-facing side 936 of the tibial bone anchoring component 916 may have a plurality of posts 990 that protrude into the bone from a transverse surface 992 oriented generally transverse to the tibia. Optionally, other bone anchoring features, as known in the art, may be used in addition to or in the alternative to the posts 990.

For example, in addition to the posts 990, the bone-facing side 936 of the tibial bone anchoring component 916 may also have stem receiver 994 positioned proximate the center of the bone-facing side 936. The stem receiver 994 may have an aperture 996 that can receive an anchoring element such as an intramedullary stem (not shown). Such an intramedullary stem may have a proximal end that can be inserted into and secured within the aperture 996, and a distal end that can be inserted into the intramedullary canal of the tibia to provide supplemental fixation of the tibial bone anchoring component 916 relative to the tibia. The stem receiver 994 may have a generally tubular shape oriented generally parallel to the tibia, and perpendicular to the transverse surface 992.

The tibial bone anchoring component 916 may further have flanges 998 that connect the side walls of the stem receiver 994 to the transverse surface 992. The flanges 998 may have crenellated shapes as shown, that present greater surface area to the interior of the tibia, thereby enhancing fixation of the tibial bone anchoring component to the tibia.

In some embodiments, the tibial bone anchoring component 916 may not, in its entirety, be made via additive manufacturing. Rather, the majority of the tibial bone anchoring component 916 may be generally made via more traditional methods such as casting, milling, and forging. The tibial bone anchoring component 916 may have a bone engagement pad 970 that is made separately from the remainder of the tibial bone anchoring component 916, and has a highly textured and/or porous shape that facilitate bone in-growth. In some embodiments, the bone engagement pad 970 may have nano-textured surfaces with features such as titanium nanotubes that provide enhanced bone engagement.

As shown, the bone engagement pad 970 may be secured to certain bone-facing surfaces of the main body of the tibial bone anchoring component 916. For example, the bone engagement pad 970 may include a transverse portion 982 that covers substantially the entirety of the transverse surface 992, post portions 980 that cover the proximal portions of the posts 990, and flange portions 988 that cover the proximal portions of the flanges 998. The posts 990, stem receiver 994, and flanges 998 may extend through apertures 999 formed in the transverse portion 982. The post portions 980 and the flange portions 988 may protrude from the transverse portion 982 and may connect to the transverse portion 982 at the peripheries of the apertures 999 through which the posts 990 and flanges 998 pass, respectively.

The post portions 980 and the flange portions 988 may be called "protruding portions," because they protrude from the transverse portion 982, and thence, from the underlying transverse surface 992. The protruding portions may also extend generally perpendicular to the transverse portion 982. "Generally perpendicular" means that the protruding portions extend along the adjacent surfaces (i.e., surfaces that are adjacent to the transverse surface) of typical bone engagement features (such as spikes, posts, keels, teeth, and/or the like) that protrude away from the transverse surface of the implant. Many such bone engagement features will have adjacent surfaces that extend perpendicular to the transverse surface, just as the posts 990, the stem receiver 994, and the flanges 998 extend perpendicular to the transverse surface 992. However, some such bone engagement features may have adjacent surfaces that are not precisely perpendicular to the transverse surface. For example, a bone anchoring feature may have a tapered (for example, conical or pyramidal) shape that causes its adjacent surface(s) extend from the transverse surface at an angle of less than 90°. A bone engagement pad may have a "protruding portion" that extends along such a surface, even though it is not precisely perpendicular to the transverse portion 982.

The bone engagement pad 970 may be made via additive manufacturing through the use of any of the methods mentioned previously. In the alternative, different methods may be used to manufacture the bone engagement pad 970 with the desired porous and/or textured shape.

In some embodiments, the bone engagement pad 970 may be relatively thin compared to the main body of the tibial bone anchoring component 916. For example, the bone engagement pad 970 may have a thickness within the range of 0.1 mm to 5 mm. More precisely, the bone engagement pad 970 may have a thickness within the range of 0.2 mm to 2 mm. Yet more precisely, the bone engagement pad 970 may have a thickness within the range of 0.5 mm to 1.5 mm. Still more precisely, the bone engagement pad 970 may have a thickness within the range of 0.8 mm to 1.2 mm. Yet more precisely, the bone engagement pad 970 may have a thickness of about 1 mm.

The bone engagement pad 970 may be formed as a single piece, such that the post portions 980, the transverse portion 982, and the flange portions 988 are all formed as a single piece with each other. In the alternative, the post portions 980, the transverse portion 982, and the flange portions 988 may be formed separately and secured together and/or simply secured to the main body of the tibial bone anchoring component 916.

The bone engagement pad 970 may be formed separately from the main body of the tibial bone anchoring component 916. Alternatively, the bone engagement pad 970 may be formed directly on the corresponding surfaces (i.e., the transverse surface 992, the posts 990, and the flanges 998) of the tibial bone anchoring component 916. In either case, the bone engagement pad 970 may be secured to the corresponding bone engagement surfaces of the tibial bone anchoring component 916 via various methods, such as diffusion bonding and/or through the use of a substance, such as the substance 340 referenced previously, which may be applied to one or both of the surfaces to be secured together to facilitate chemical and/or adhesive bonding. In some embodiments, a paste including a metallic powder, such as Titanium nanoparticles, may be used to facilitate diffusion bonding, melting together of the surfaces to be attached, and/or other attachment mechanisms. Alternatively or additionally, various welding techniques such as laser welding, friction welding, and/or the like may be used.

In some embodiments, the bone engagement pad 970 may have a non-uniform structure that presents different surface properties to the bone and the corresponding bone engagement surfaces of the tibial bone anchoring component 916 to which it is attached. For example, the bone engagement pad 970 may have a bone-facing surface with a high level of porosity and/or surface texturing to provide secure bone engagement and/or in-growth. The bone engagement pad 970 may further have a joint-facing surface secured to the corresponding bone engagement surfaces of the tibial bone anchoring component 916, with a lower level of porosity and/or surface texturing to facilitate secure attachment of the bone engagement pad 970 to the corresponding bone engagement surfaces of the tibial bone anchoring component 916.

In some embodiments, the porosity of the bone engagement pad 970 may have a gradient through the thickness of the bone engagement pad 970, from a highly-porous state at the bone-facing surface of the bone engagement pad 970, to a much less porous state at the joint-facing surface. In alternative embodiments, the change in porosity may be less gradual (i.e., "stepped."). For example, additional material may be added to the joint-facing surface of the bone engagement pad 970 and melted, fused, and/or otherwise used to fill the pores in the joint-facing surface so that a layer exists on the joint-facing side in which the porosity is much lower than in the remainder of the bone engagement pad 970. In either case, the result may be that the joint-facing surface of the bone engagement pad 970 is much smoother than the bone engagement surface of the bone engagement pad 970, allowing the joint-facing surface to more readily and securely attach to the corresponding bone engagement surfaces of the tibial bone anchoring component 916, while retaining the enhanced bone in-growth of a porous structure in the bone engagement surface of the bone engagement pad 970.

Figure 10:
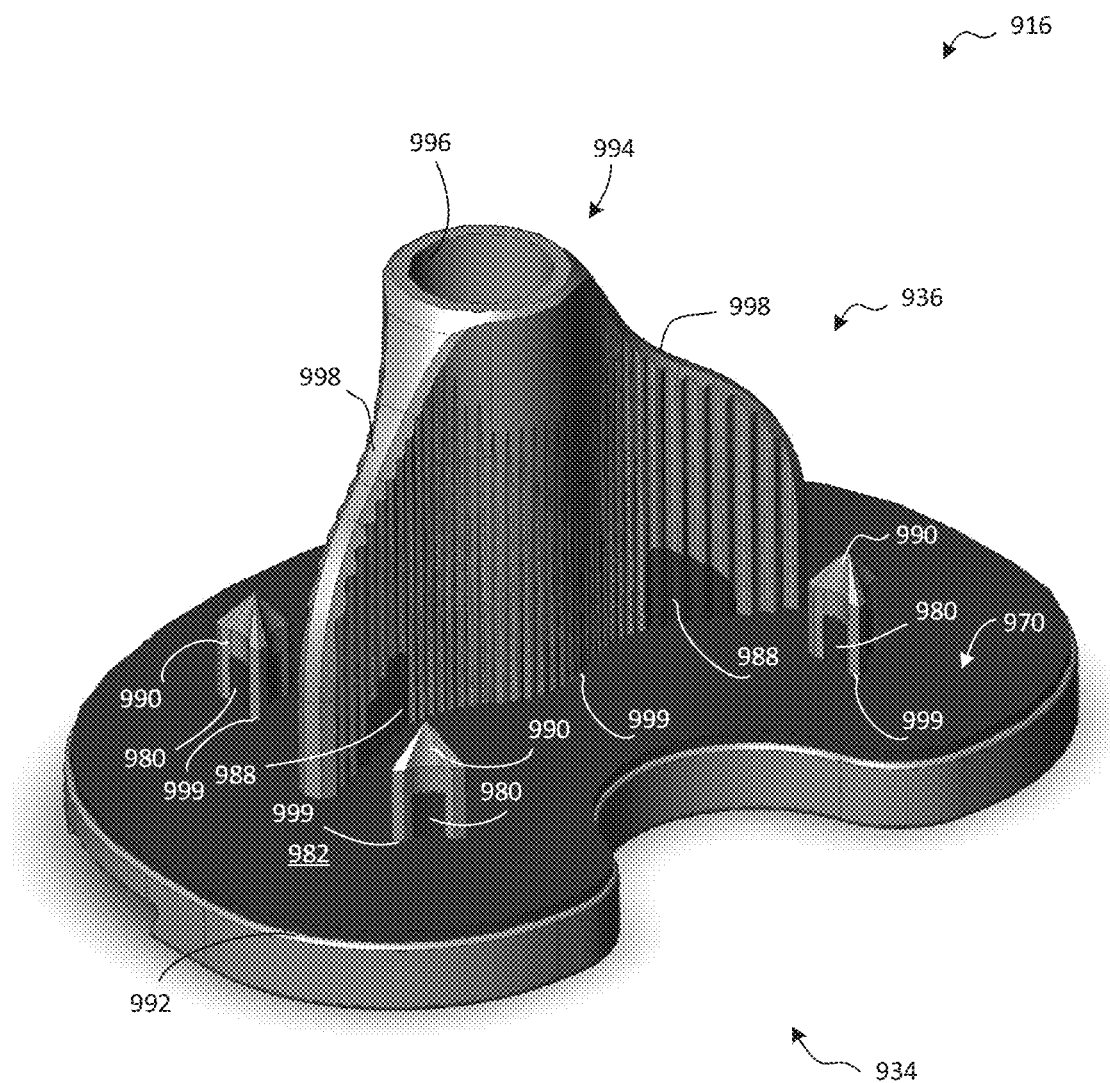
FIG. 10 is a perspective view, from a different viewpoint, of the tibial bone anchoring component of FIG. 9.

FIG. 10 is a perspective view, from a different viewpoint, of the tibial bone anchoring component 916 of FIG. 9. FIG. 10 depicts the positioning of flange portions 988 on both sides of the flanges 998 of the tibial bone anchoring component 916. Of course, this is merely exemplary. Those of skill in the art will recognize that the bone engagement pad 970 may be reconfigured in a wide variety of alternative configurations.

For example, in some configurations, the post portions 980 may extend to cover more or less of the posts 990, or may be omitted altogether. Similarly, the flange portions 988 may extend to cover more or less of the flanges 998, or may be omitted altogether. One or more stem receiver portions (not shown) may be added to cover some portion(s) of the exterior-facing surfaces of the stem receiver 994, adjacent to the transverse portion 982. Yet further, in other alternative embodiments, the bone engagement pad 970 may include a stem portion (not shown) that covers some or all of the stem (not shown). Such protruding portions may have thicknesses that are greater than, less than, and/or equal to the thickness of the transverse portion 982. Further, the transverse portion 982 may extend to cover more or less of the transverse surface 992, or may be omitted altogether.

Further, those of skill in the art will recognize that the same principles may be applied to a femoral component. Specifically, a femoral component (not shown) according to an alternative embodiment may include a bone engagement pad that covers one or more bone-facing surfaces, including planar surfaces, post surfaces, and/or other bone-engaging surfaces.

Yet further, those of skill in the art will recognize that the same principles may be applied to any implant for which secure bone engagement is desired. A bone engagement pad, consisting of one or more portions that may be separately formed or formed as a single piece with each other, may be secured to one or more bone-facing surfaces of an implant for arthroplasty, fusion, or modification of any joint, or for replacement of hard tissue such as a tooth or jaw.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. Elements not so recited are not intended to be so construed. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A prosthesis for replacing a natural articular surface on bone, the prosthesis comprising:
   a joint facing side comprising an articular surface;
   a bone anchoring side comprising a bone engagement surface; and
   a bone engagement pad secured to at least part of the bone engagement surface, the bone engagement pad comprising:
   a pad bone-facing surface comprising a first porosity level; and
   a pad joint-facing surface comprising a second porosity level lower than the first porosity level;
   wherein the bone engagement surface is formed via a first manufacturing process; and the bone engagement pad is formed via a second manufacturing process different from the first manufacturing process, and wherein the first and second porosity levels of the bone engagement pad are formed during the second manufacturing process;
   wherein the bone engagement pad comprises a transverse portion configured to extend transverse to a length of the bone, the pad bone-facing surface and the pad joint-facing surface are on opposite sides of the bone engagement pad, and the transverse portion comprises a porosity gradient by which porosity of the transverse portion gradually increases toward the pad bone-facing surface.

2. The prosthesis of claim 1, wherein: the first manufacturing process is selected from the group consisting of forging, milling, and casting; and the second manufacturing process is an additive manufacturing process.

3. The prosthesis of claim 2, wherein: the second manufacturing process is 3D printing.

4. The prosthesis of claim 1, wherein the bone engagement pad has a thickness within the range of 0.5 mm to 1.5 mm.

5. The prosthesis of claim 1, wherein
   the transverse portion has a thickness, parallel to the length, that is uniform.

6. The prosthesis of claim 1, wherein the bone engagement pad comprises:
   one or more protruding portions extending perpendicular to the transverse portion.

7. The prosthesis of claim 6, wherein: the bone engagement surface comprises a bone engagement feature extending through an aperture formed in the transverse portion; and
   the one or more protruding portions extend from one or more edges of the aperture, alongside one or more surfaces of the bone engagement feature.

8. The prosthesis of claim 1, wherein: the prosthesis comprises a knee implant;
   the articular surface is configured to a shape to replace the natural articular surface; and
   the natural articular surface is one of a natural tibial surface and a natural femoral articular surface.

9. The prosthesis of claim 1, wherein: the bone engagement surface comprises a bone engagement feature extending through an aperture formed in the bone engagement pad.

10. A prosthesis for replacing a natural articular surface on bone, the prosthesis comprising:
- a joint facing side comprising an articular surface;
- a bone anchoring side comprising a bone engagement surface; and
- a bone engagement pad secured to at least part of the bone engagement surface, the bone engagement pad comprising:
  - a transverse portion configured to extend transverse to a length of the bone; and
  - wherein the bone engagement pad has a thickness within the range of 0.5 mm to 1.5 mm;
  - wherein the bone engagement pad comprises a pad bone-facing surface and a pad joint-facing surface on opposite sides of the bone engagement pad, and the transverse portion comprises a porosity gradient by which porosity of the transverse portion gradually increases toward the pad bone-facing surface.

11. The prosthesis of claim 10, wherein: the bone engagement surface is formed via a first manufacturing process; and the bone engagement pad is formed via a second manufacturing process different from the first manufacturing process.

12. The prosthesis of claim 11, wherein: the first manufacturing process is selected from the group consisting of forging, milling, and casting; and the second manufacturing process is an additive manufacturing process.

13. The prosthesis of claim 10, wherein the thickness is parallel to the length and is uniform.

14. The prosthesis of claim 10, wherein: the prosthesis comprises a knee implant;
- the articular surface is configured to a shape to replace the natural articular surface; and
- the natural articular surface is one of a natural tibial surface and a natural femoral articular surface.

15. The prosthesis of claim 10, wherein:
the
- the transverse portion has a thickness, parallel to the length, that is uniform.

16. The prosthesis of claim 10, wherein:
- the bone engagement pad further comprises one or more protruding portions extending generally perpendicular to the transverse portion.

17. The prosthesis of claim 16, wherein: the bone engagement surface comprises a bone engagement feature extending through an aperture formed in the transverse portion; and the one or more protruding portions extend from one or more edges of the aperture, alongside one or more surfaces of the bone engagement feature.

18. The prosthesis of claim 10, wherein: the prosthesis comprises a knee implant and the articular surface is configured to replace the natural articular surface.

19. A prosthesis for replacing a natural articular surface on bone, the prosthesis comprising:
- a joint facing side comprising an articular surface;
- a bone anchoring side comprising a bone engagement surface; and
- a bone engagement pad secured to at least part of the bone engagement surface, the bone engagement pad comprising:
  - a transverse portion configured to extend transverse to a length of the bone, a pad bone-facing surface and a pad joint-facing surface are on opposite sides of the bone engagement pad, and the transverse portion comprises a porosity gradient by which porosity of the transverse portion gradually increases toward the pad bone-facing surface;
  - wherein: the bone engagement surface comprises one or more bone engagement features extending through one or more corresponding apertures formed in the transverse portion.

20. The prosthesis of claim 19, wherein: the transvers portion comprises one or more protruding portions corresponding to the one or more bone engagement features.

21. The prosthesis of claim 20, wherein: the one or more protruding portions extend from one or more edges of the one or more corresponding apertures, alongside one or more surfaces of the one or more bone engagement features.

22. The prosthesis of claim 19, wherein the bone engagement pad has a thickness within the range of 0.5 mm to 1.5 mm.

23. The prosthesis of claim 19, wherein the bone engagement surface is formed via a first manufacturing process; and the bone engagement pad is formed via a second manufacturing process different from the first manufacturing process.

24. The prosthesis of claim 23, wherein the transverse portion comprises:
- the pad bone-facing surface comprising a first porosity level; and
- the pad joint-facing surface comprising a second porosity level lower than the first porosity level;
- and wherein the first and second porosity levels of the transverse portion are formed during the second manufacturing process.

25. The prosthesis of claim 24, wherein: the second manufacturing process is 3D printing.

* * * * *